US006838593B2

(12) United States Patent
Garnaat et al.

(10) Patent No.: US 6,838,593 B2
(45) Date of Patent: Jan. 4, 2005

(54) AUSTIN RESPONSIVE PROMOTER SEQUENCES AND METHODS OF USING THE SAME

(75) Inventors: Carl W. Garnaat, Ankeny, IA (US); Keith S. Lowe, Johnston, IA (US); Bradley A. Roth, Urbandale, IA (US)

(73) Assignee: Pioneer Hi-Bred Int'l Inc., Des Moines, IA (US)

( * ) Notice: Subject to any disclaimer, the term of this patent is extended or adjusted under 35 U.S.C. 154(b) by 0 days.

(21) Appl. No.: 09/905,558

(22) Filed: Jul. 13, 2001

(65) Prior Publication Data

US 2003/0024004 A1 Jan. 30, 2003

Related U.S. Application Data

(60) Provisional application No. 60/217,942, filed on Jul. 13, 2000.

(51) Int. Cl.$^7$ .................. C12N 15/09; C12N 15/82; A01H 5/00; A01H 5/10
(52) U.S. Cl. .................. 800/287; 800/278; 800/295; 435/320.1; 435/419; 435/468; 536/24.1
(58) Field of Search .................. 800/287, 278, 800/295, 286, 298; 435/320.1, 419, 468, 69.1; 536/24.1, 23.6, 24.5

(56) References Cited

U.S. PATENT DOCUMENTS

| | | | | |
|---|---|---|---|---|
| 5,795,753 A | * | 8/1998 | Cigan et al. | 435/172.3 |
| 5,986,174 A | | 11/1999 | Barbour et al. | 800/287 |
| 6,222,095 B1 | | 4/2001 | Callis et al. | 800/278 |
| 6,235,975 B1 | | 5/2001 | Harada et al. | 800/306 |
| 6,245,717 B1 | | 6/2001 | Dean et al. | 504/321 |
| 6,252,139 B1 | | 6/2001 | Doerner et al. | 800/290 |
| 6,268,552 B1 | | 7/2001 | Li | 800/317.4 |

FOREIGN PATENT DOCUMENTS

| | | | | |
|---|---|---|---|---|
| WO | WO 96/17945 | 6/1996 | ........... | C12N/15/82 |
| WO | WO97/18310 | 5/1997 | ........... | C12N/15/29 |
| WO | WO98/37184 | 8/1998 | ........... | C12N/15/00 |
| WO | WO99/46396 | 9/1999 | ........... | C12N/15/82 |
| WO | WO 99/64579 | 12/1999 | ........... | C12N/15/00 |
| WO | WO 00/28058 | 5/2000 | ........... | C12N/15/82 |
| WO | WO01/18170 A2 | 3/2001 | | |
| WO | WO 01/83790 | 11/2001 | ........... | C12N/15/82 |

OTHER PUBLICATIONS

Kim et al. Plant Mplecular Biology, vol. 24, pp. 105–117, 1994.*
Benfey et al. Science, vol. 250, pp. 959–966, 1990.*
Extoxnet Extension Toxicology Network Pesticide Information Profiles, "Dicamba", Oregon State University, Jun. 1996.
Abel, et al., "The PS–IAA4/5–like Family of Early Auxin–inducible mRNAs in Arabidopsis thaliana", Journal of Molecular Biology, vol. 251, pp. 533–549, 1995.
Bruce, et al., "Expression profiling of the maize flavonoid pathway genes controlled by estradiol–inducible transcription factors CRC and P", The Plant Cell, vol. 12, pp. 65–79, Jan. 2000.
Guilfoyle, "Aux/IAA proteins and auxin signal transduction", Trends in Plant Science, vol. 3, No. 6, pp. 205–207, Jun. 1998.
Guilfoyle, "Auxin–regulated genes and promoters", Biochemistry and Molecular Biology of Plant Hormones, pp. 423–459, 1999.
Guilfoyle, et al., "How does auxin turn on genes?", Plant Physiology, vol. 118, pp. 341–347, 1998.
Guilfoyle, et al., "Potential use of hormone–responsive elements to control gene expression in plants", Inducible Gene Expression in Plants,pp. 219–2326, 1999.
Liu, et al., "Soybean GH3 promoter contains multiple auxin–inducible elements", The Plant Cell, vol. 6, pp. 645–657, May 1994.
Lu, et al., "Sugar response sequence in the promoter of a rice α–amylase gene serves as a transcriptional enhancer", The Journal of Biological Chemistry, vol. 273, No. 17, pp. 10120–10131, Apr. 24, 1998.
Park, et al., "Tissue–specific expression of AUX1 in maize roots", 42$^{nd}$ Annual Maize Genetics Conference, Coeur d'Alene, Idaho, Mar. 16–19, 2000.
Sitbon, et al., "Expression of auxin–regulated genes", Physiologia Plantarum, vol. 100; pp. 443–445, 1997.
Su, et al., "Dehydration–stress–regulated transgene expression in stably transformed rice plants", Plant Physiology, vol. 117, pp. 913–922, 1998.
Takahashi, et al., "Auxin–regulated genes", Plant Cell Physiol., vol. 36(3), pp. 383–390, 1995.
Ulmasov, et al., "Activation and repression of transcription by auxin–responsive factors", Proc. Natl. Acad. Sci. USA, vol. 96, pp. 5844–5849, May 1999.
Ulmasov, et al., "Dimerization and DNA binding of auxin response factors", The Plant Journal, vol. 19(3), pp. 309–319, 1999.
Walker, et al., "Molecular mechanisms of auxin action", Plant Biology, vol. 1, pp. 434–439, 1998.
Li, et al., "An auxin–responsive promoter is differentially induced by auxin gradients during tropisms", The Plant Cell, vol. 3, pp. 1167–1175, Nov. 1991.
Oeller, et al., "Structural characterization of the early indoleacetic acid–inducible genes, PS–IAA4/5 and PS–IAA6, of pea (pisum sativum L.)", Journal Molecular Biology, vol. 233, ppg. 789–798, 1993.
Qiu, et al., "Expressed sequence tags from B73 maize seedlings and silks", Database accession No. BG841066.
Walbot, V., "Maize ESTs from various cDNA libraries sequenced at Stanford University", Database accession No. AW787286.

* cited by examiner

Primary Examiner—Amy J. Nelson
Assistant Examiner—Medina A. Ibrahim
(74) Attorney, Agent, or Firm—Pioneer Hi-Bred, Int'l Inc.

(57) ABSTRACT

The invention provides isolated auxin-responsive transcriptional regulatory elements and polynucleotides associated therewith. The present invention provides methods and compositions related to altering gene expression in plants. The invention further provides recombinant expression cassettes, host cells, and transgenic plants.

8 Claims, 12 Drawing Sheets

; GAP of: W0h051-7.Seq  check: 6926  from: 1  to: 52 seq of dicamba induced band w0c0 51.7 to: Cjlpi81r.Seq  check: 2737  from: 1  to: 714

Symbol comparison table: Gencoredisk:[Gcgcore.Data.Rundata]Nwsgapdna.Cmp
CompCheck: 8760

```
    Gap Weight:        50        Average Match:    10.000
 Length Weight:         3        Average Mismatch:  0.000

Quality:       520               Length:      714
         Ratio:    10.000                 Gaps:        0
 Percent Similarity: 100.000   Percent Identity: 100.000

Match display thresholds for the alignment(s):

| = IDENTITY
             : =
             . =

W0h051-7.Seq x Cjlpi81r.Seq..

1 ........................gctagctgcgccgtgaccacgcacat                26
                           |||||||||||||||||||||||||||
 1 CGATCGAAGTGGGTGTGTCAGTAGCTAGCTGCGCCGTGACCACGCACAT                 50

27 gaccgcagtgcgcgcggggctgatca....................                   52
   |||||||||||||||||||||||||||
51 GACCGCAGTGCGCGCGGGGCTGATCAAGGGAAAGTGATCGGATGGAGCTG               100
```

Figure 2

```
ZmAxig1       DOMAIN I                                    NLS
          1   MELELGLAPPNPHQPLAAAAEFVGLLSSSAGSCGNKRVLGDAFGAAKAAT    50
              ||  ||||  |                |   : |       ||
PS-IAA4/5 1   mefkatelrlgl.pg......iteeeekkiihgssvvknnnkr.........  36

DOMAIN II.         NLS
          51  LPLFVCEDGDGDGGGDRDRDGVVDHEQQSNNVPRKKRLVGWPPVKCARRRS  100
              : |       | ::    ||||  :: :||||||    |:.  |
          35  qlpqtseesvsiskvtndehi.vesssaappakakivgwppirsyrkns    84

.DOMAIN III
          101 ......CGGGGYVKVKLEGVPIGRKVDVSIHGSYQELLRTLESMFPSGNQQD  145
                    :|||   |::|  |||:|  :|   ||  |  |||:|.
          85  lheadvggifvkvsmdgapylrkidlrvyggvsellkaletmfkl.tige   133
                                β    α

.DOMAIN IV.       NLS
          146 HAEDEVVVSHERRRRHPYVVTYEDGEGDWLLVGDDVPWEVFVVKSVKRLKI  195
              : :              |  |||     :|||::||:||::||  |||:|
          134 yseregykgse......yaptyedkdgdwmlvg.dvpwdmfvtsckrlri   176

196 LA............   197
              :
          177 mkgteakglgcgv     189
```

```
GAP of: Czaal47.Seq  check: 446  from: 1  to: 1214
   to: Axiglcomplete.Con  check: 928  from: 1  to: 3123

Symbol comparison table:
Gencoredisk:[Gcgcore.Data.Rundata]Nwsgapdna.Cmp
  CompCheck: 8760

Gap Weight:       50     Average Match:   10.000
         Length Weight:        3     Average Mismatch: 0.000

Quality:    10871             Length:     3123
                 Ratio:    8.955               Gaps:        3
    Percent Similarity:  100.000     Percent Identity: 100.000

Match display thresholds for the alignment(s):
                       | = IDENTITY
                       : = 5
                       . = 1

Czaal47.Seq x Axiglcomplete.Con  May 11, 2000 12:05  ..

1 ..............................GCAGGAACTTAT 12
                                    ||||||||||||
 1101 CGCGTCACTCACGGGTAGCTCATGGTCGAGCGTAGCATGCAGGAACTTAT 1150

13 TTGCCGTGCGCTCCCAGGTCTCCGCTCGCGTGCCTTCCAGTCTGTCTCAC 62
      ||||||||||||||||||||||||||||||||||||||||||||||||||
 1151 TTGCCGTGCGCTCCCAGGTCTCCGCTCGCGTGCCTTCCAGTCTGTCTCAC 1200

63 ACTAGCTGCTGTGGGACGATCGAAGTGGGTGTGTCAGCTAGCTAGCTGCG 112
      ||||||||||||||||||||||||||||||||||||||||||||||||||
 1201 ACTAGCTGCTGTGGGACGATCGAAGTGGGTGTGTCAGCTAGCTAGCTGCG 1250

113 CCGTGACCACGCACATGACCGCAGTGCGCGCGGGGCTGATCAAGGGAAAG 162
      ||||||||||||||||||||||||||||||||||||||||||||||||||
 1251 CCGTGACCACGCACATGACCGCAGTGCGCGCGGGGCTGATCAAGGGAAAG 1300

163 TGATCGGATGGAGCTGGAGCTCGGGCTCGCGCCGCCGAACCCGCATCAGC 212
      ||||||||||||||||||||||||||||||||||||||||||||||||||
 1301 TGATCGGATGGAGCTGGAGCTCGGGCTCGCGCCGCCGAACCCGCATCAGC 1350

213 CGCTGGCTGCCGCCGCCGAGTTCGTCGGTCTCCTCAGCAGCTCGGCTGGC 262
      ||||||||||||||||||||||||||||||||||||||||||||||||||
 1351 CGCTGGCTGCCGCCGCCGAGTTCGTCGGTCTCCTCAGCAGCTCGGCTGGC 1400

263 TCGTGCGGGAACAAGAGGGTTCTCGGCGACGCGTTCGGGGCCGCCAAGGC 312
      ||||||||||||||||||||||||||||||||||||||||||||||||||
 1401 TCGTGCGGGAACAAGAGGGTTCTCGGCGACGCGTTCGGGGCCGCCAAGGC 1450

313 GGCCACGCTTCCGCTCTTCGTCTGCGAGGATGGCGACGGAGGCGGCGGCG 362
      ||||||||||||||||||||||||||||||||||||||||||||||||||
 1451 GGCCACGCTTCCGCTCTTCGTCTGCGAGGATGGCGACGGAGGCGGCGGCG 1500
```

```
 363 ACCGCGACCGCGACGGCGTCGTCGACCATGAACAGCAAAGCAACAA.... 408
     ||||||||||||||||||||||||||||||||||||||||||||||
1501 ACCGCGACCGCGACGGCGTCGTCGACCATGAACAGCAAAGCAACAAGTGA 1550

409 .......................TGTACCCAGGAAGAAGAGGCTGG 431
                            ||||||||||||||||||||||||
1601 CCCAAATCCGATCCGTGGTGTGTGTAGTGTACCCAGGAAGAAGAGGCTGG 1650

432 TGGGGTGGCCGCCGGTGAAGTGCGCGCGTAGGCGTAGCTGCGGCGGCGGG 481
     |||||||||||||||||||||||||||||||||||||||||||||||||
1651 TGGGGTGGCCGCCGGTGAAGTGCGCGCGTAGGCGTAGCTGCGGCGGCGGG 1700

482 TACGTGAAGGTGAAGCTGGAAGGGGTGCCCATCGGGCGGAAGGTGGACGT 531
     |||||||||||||||||||||||||||||||||||||||||||||||||
1701 TACGTGAAGGTGAAGCTGGAAGGGGTGCCCATCGGGCGGAAGGTGGACGT 1750

532 GTCCATCCACGGCTCGTACCAGGAGCTGCTCCGCACGCTCGAGAGCATGT 581
     |||||||||||||||||||||||||||||||||||||||||||||||||
1751 GTCCATCCACGGCTCGTACCAGGAGCTGCTCCGCACGCTCGAGAGCATGT 1800

582 TCCCTTCGGGTAACCAACA............................ 600
     |||||||||||||||||||
1801 TCCCTTCGGGTAACCAACAAGGTGCGTACGTTCCCGGGCCGCGGCGAGCC 1850

601 ..............................................AG 602
                                                   ||
1951 CTCCCGGCACTTAACTTGGTCGCATATACTATTCCTGTAACCTCTGGCAG 2000

603 ATCATGCAGAAGACGAGGTGGTGGTCTCGCACGAGCGCCGCCGTCGCCAT 652
     |||||||||||||||||||||||||||||||||||||||||||||||||
2001 ATCATGCAGAAGACGAGGTGGTGGTCTCGCACGAGCGCCGCCGTCGCCAT 2050

653 CCTTATGTAGTCACCTACGAGGACGGCGAAGGGGACTGGTTGCTCGTCGG 702
     |||||||||||||||||||||||||||||||||||||||||||||||||
2051 CCTTATGTAGTCACCTACGAGGACGGCGAAGGGGACTGGTTGCTCGTCGG 2100

703 AGATGATGTGCCGTGGGA............................ 720
     ||||||||||||||||||
2101 AGATGATGTGCCGTGGGAGTACGTATCAGTCACTACTACTGTCGTCTGTA 2150

721 ........................GGTCTTTGTCAAGTCAGTG 739
                             |||||||||||||||||||
2201 GAACTTAAAAACGACGTTGATTTCCTTGCAGGGTCTTTGTCAAGTCAGTG 2250

740 AAGCGGCTCAAGATACTTGCGTAGCCGACGGTCGGCGCCTCAGAGACGTC 789
     |||||||||||||||||||||||||||||||||||||||||||||||||
2251 AAGCGGCTCAAGATACTTGCGTAGCCGACGGTCGGCGCCTCAGAGACGTC 2300
```

```
 790 GTGTGGTCCGTCTCACCAGGATCGGAGCAGTGTAGTACTCCTGGGCGTCA  839
     ||||||||||||||||||||||||||||||||||||||||||||||||||
2301 GTGTGGTCCGTCTCACCAGGATCGGAGCAGTGTAGTACTCCTGGGCGTCA 2350

840 TCTGCGTAATAACGTTGTTTCTGTCCTGTGTGCCCGTAGCAGTACGTACT  889
     ||||||||||||||||||||||||||||||||||||||||||||||||||
2351 TCTGCGTAATAACGTTGTTTCTGTCCTGTGTGCCCGTAGCAGTACGTACT 2400

890 GTCCTATAGTAAGCTAGCTTTATGGGGTGCTTCAGCTTTCAGAGCATGAC  939
     ||||||||||||||||||||||||||||||||||||||||||||||||||
2401 GTCCTATAGTAAGCTAGCTTTATGGGGTGCTTCAGCTTTCAGAGCATGAC 2450

940 GAAAGCACTGATTAGCTGCTGTCATCACATTTGGTTCGTCTTTGTGTCGT  989
     ||||||||||||||||||||||||||||||||||||||||||||||||||
2451 GAAAGCACTGATTAGCTGCTGTCATCACATTTGGTTCGTCTTTGTGTCGT 2500

990 ACGGTATCGCTGGCGTCAGTGTCGCGGCAGCCTAGGTGATCTAAGCATAC 1039
     ||||||||||||||||||||||||||||||||||||||||||||||||||
2501 ACGGTATCGCTGGCGTCAGTGTCGCGGCAGCCTAGGTGATCTAAGCATAC 2550

1040 TTACTATCTCAAGTTACTTTTGGTTTCCTGAGCTTGCATGGTAATTCATA 1089
     ||||||||||||||||||||||||||||||||||||||||||||||||||
2551 TTACTATCTCAAGTTACTTTTGGTTTCCTGAGCTTGCATGGTAATTCATA 2600

1090 TACCGTATACGTGTGTGACTCAGGGGCGAAGCTGCCTTAAGGCACAGGGG 1139
     ||||||||||||||||||||||||||||||||||||||||||||||||||
2601 TACCGTATACGTGTGTGACTCAGGGGCGAAGCTGCCTTAAGGCACAGGGG 2650

1140 TCACCGGACCCGATGGAATTTATCAAATCCAGTGTAAAATACTATTTAAC 1189
     |||||||||||||||||||||||.||||||||||||||||||||||||||
2651 TCACCGGACCCGATGGAATTTATCAAATCCAGTGTAAAATACTATTTAAC 2700

1190 ACTGTTCATCAATATATTTGATTTC......................... 1214
     |||||||||||||||||||||||||
2701 ACTGTTCATCAATATATTTGATTTCAATAATTCATGGAGCTGACCTTGTG 2750
```

| Sequence Name | SEQ ID NO: | ATCC Deposit |
|---|---|---|
| Pioneer clone CZAAL47 | 1 | PTA-2426 |
| ZmAxig1 polypeptide | 2 | |
| Native ZmAxig1 promoter region | 3 | |
| Modified ZmAxig1 promoter region | 4 | PTA-2427 |
| A632 full-length ZmAxig1, including SEQ ID No. 3 | 5 | PTA-2426 PTA-2427 |
| Primer 1, used for isolation of 5'flanking region | 6 | |
| Primer 2, used for isolation of 5'flanking region | 7 | |
| Primer 3, used for isolation of region spanning start codon | 8 | |
| Primer 4, used for isolation of region spanning start codon | 9 | |
| Primer 5, used for isolation of 5' region | 10 | |
| Oligonucleotide designed to remove clones having a poly-A tail but no cDNA | 11 | |
| Pioneer clone Cjlpi81 | 12 | |
| CuraGen fragment w0h051.7 | 13 | |
| Primer 6, used to isolate the coding sequence and 3' region | 14 | |
| Primer 7, used to isolate the coding sequence and 3' region | 15 | |
| Modified ZmAxig1 promoter region with single-base deletion | 16 | PTA-2427 |
| LEC1 transcriptional activator element | 17 | |
| LEC1 polynucleotides | 18-20 | |
| LEC1 polypeptide consensus sequence | 21 | |

Figure 10. Representative polynucleotides and polypeptides of the present invention.

| Experiment | Control | Ubi:LEC1 | Axig1:LEC1 |
|---|---|---|---|
| #1 3938.37 | 15% | 63% | 44% |
| #2 3938.79 | 4% | 17% | 20% |
| #3 3938.78 | 16% | 17% | 38% |
| #4 3938.34 | 2% | 14% | 13% |

Figure 11. Transformation frequencies by LEC1 with two different promoters. Transformation frequencies were based on the percentage of plated embryos with one or more GFP positive/Bialaphos resistant colonies. All embryos were shot with Ubi:moPAT-GFP (a construct conferring Bialaphos resistance and GFP fluorescence) along with a LEC1 construct or a control DNA.

AUSTIN RESPONSIVE PROMOTER SEQUENCES AND METHODS OF USING THE SAME

CROSS-REFERENCE TO RELATED APPLICATIONS

This application claims priority to, and hereby incorporates by reference, provisional patent application No. 60/217,942, filed Jul. 13, 2000.

TECHNICAL FIELD

The present invention relates generally to plant molecular biology. More specifically, it relates to nucleic acids and methods for modulating their expression in plants, and especially to novel regulatory elements which confer chemically-inducible, tissue-preferred gene expression. More specifically, the present invention is directed to a tissue-preferred regulatory element which is responsive to auxins, and to the use of said regulatory element. This invention is also directed to the native structural gene associated with said regulatory element in Zea mays.

BACKGROUND OF THE INVENTION

Auxin Responsiveness

Auxins are a group of chemicals which act as plant growth regulators. The class includes, for example, natural compounds such as indole-3-acetic acid (IAA), as well as synthetic auxins such as dicamba, clopyralid, 2,4-dichlorophenoxyacetic acid (2,4-D), and 2,4,5-trichloroacetic acid (2,4,5-T). Auxins are implicated in the regulation of cell extension, cell division, tropisms, vascular differentiation, apical dominance, and root formation. Most, if not all, auxin-induced growth and developmental responses involve alterations in gene expression (Guilfoyle, T. J. (1986) CRC Critical Reviews in Plant Science 4:247–276). Auxin enhances the abundance of a select and conserved set of mRNAs in various plant species, allowing study of gene expression through monitoring of mRNAs, in vitro translation, and cDNA cloning.

"Early genes", selectively induced in a primary response to auxin prior to the initiation of cell growth, are likely candidates to play a pivotal role in mediating growth-stimulating effects of the hormone. These primary-response genes are induced independent of de novo protein synthesis, indicating direct gene activation. Products of these primary-response genes serve three main functions: emergency rescue and stress adaptation; intercellular communication; and transcriptional regulation of secondary genes to establish and coordinate long-term biological consequences through cascades of auxin signaling. (Abel and Theologis (1996) Plant Physiol. 111:9–17) Thus, primary response genes are of interest both in terms of their activation in response to auxin and in terms of their gene products' downstream effects on plant growth and development.

Multi-gene families of early-auxin-responsive genes have been identified across species. The large Aux/IAA gene family includes related genes from soybean, pea, mung bean, and Arabidopsis. Each is characterized by two to four introns at conserved positions and encodes a small hydrophilic polypeptide with a molecular mass of 19 to 36 kD. (Oeller, P. W., et al. (1993) Journal of Molecular Biology 233:789–798) Aux/IAA mRNAs are specifically induced by biologically active auxins and do not respond to biologically inactive auxin analogs, other plant hormones, or environmental stress. (Guilfoyle, T. J., "Auxin-Regulated Genes and Promoters," in: Hooykaas, P. J. J., et al., *Biochemistry and Molecular Biology of Plant Hormones* (Amsterdam, Elsevier, 1999) pp. 423–453)

In contrast, the SAUR (Small Auxin Up RNA) gene family has been studied in a limited number of species. In soybean, five SAUR genes are closely clustered, do not contain introns, and encode highly similar polypeptides of 9 to 10 kD. (Abel and Theologis, supra; Guilfoyle, T. J., 1999, supra) An auxin-induced maize gene involved in coleoptile cell elongation was found to have homology to genes in the SAUR family (Knauss, T., et al., abstract, International Symposium on Auxins and Cytokinins in Plant Development, 26–30 July 1999, Prague, Czech Republic).

Still others types of auxin-responsive genes, such as ACC (1-amino-cyclopropane-1-carboxylic acid) Synthase, involved in ethylene synthesis, may be secondary response genes; i.e., expression is the result of secondary or indirect auxin effects. Several dozen other auxin-responsive cDNA clones from a range of species are less well characterized but demonstrate up- or down-regulation in response to auxin. Expression may also be tissue-specific. (See Tables 1 and 3 in Guilfoyle, T. J., 1999, supra)

A need exists for further characterization of plant responses to auxin. "The list of auxin-induced transcripts continues to grow, emphasizing the plethora of mRNAs that are induced either directly or indirectly by auxin. These mRNAs encode a number of proteins that play potential roles in auxin action and auxin-stimulated growth responses; however, none of these roles in auxin responses has been firmly established." (Guilfoyle, T. J., 1999, supra, p. 15) Indeed, "despite its critical role in plant development and the immense volume of studies on the diverse auxin effects, understanding of the molecular mechanisms of auxin action remains one of the major challenges of plant biology." (Abel and Theologis, supra)

Recent studies, including functional tests, have identified putative auxin response elements (AuxREs), conserved sequences in the promoter regions of auxin-responsive genes. Two relatively well-characterized AuxREs are the ocs/as-1 element and the TGTCNC element.

The ocs/as-1 AuxRE was originally identified as an enhancer element in the promoter of the *Agrobacterium tumefaciens* octopine synthase gene (Ellis et al. (1987) EMBO Journal 6:3203–3208), and similar sequences were subsequently found in the promoter regions of several plant DNA viruses and of soybean and tobacco glutathione S-transferase (GST) genes. It is noted that GST genes may respond not only to exogenous auxins but also to a variety of other hormones, chemical agents, pathogens, and wounding. (Guilfoyle and Hagen, "Potential Use of Hormone-responsive Elements to Control Gene Expression in Plants," in *Inducible Gene Expression* (CAB International, 1999)) The element is a 20-bp DNA sequence that consists of an 8-bp direct repeat separated by 4 bp; it has been shown to respond to both biologically active auxins (e.g., IAA, alpha-NAA, 2,4-D, 2,4,5-T) and biologically inactive or weak auxin analogs (e.g., 2,3-D, 2,5-D, 2,6-D, 3,4-D, 3,5-D, 2,4,6-T, and beta-NAA). (see Guilfoyle and Hagen, supra)

In contrast, in the soybean GH3 gene, a composite of two adjacent or overlapping elements, a constitutive element and a TGTCTC element, function in combination to confer responsiveness to biologically active auxins only. (Guilfoyle & Hagen, supra, p. 223) (Guilfoyle, supra, p. 28) Variation in the combination can result in temporal, tissue, and/or developmental specificity of hormone-induced expression for a particular gene. Synthetic composite AuxREs further indicate that the TGTCTC element might function as a global AuxRE within plant genomes and could be coupled with a variety of constitutive elements.

Further identification and characterization of auxin-responsive elements in crop species would be useful in refining control of plant growth and development.

Promoters

Expression of heterologous DNA sequences in a plant host is dependent upon the presence of an operably-linked promoter that is functional within the plant host. Choice of the promoter sequence will determine when and where within the organism the heterologous DNA sequence is expressed.

Where continuous expression is desired throughout the cells of a plant, constitutive promoters are utilized. Examples of constitutive promoters include the cauliflower mosaic virus (CaMV) 35S transcription initiation region, the Nos, 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the pEmu promoter, the rubisco promoter, the GRP1–8 promoter, and other transcription initiation regions from various plant genes known to those of skill.

Alternatively, the plant promoter can direct expression of a polynucleotide of the present invention in a specific tissue or may be otherwise under more precise environmental or developmental control. Where gene expression in response to a stimulus is desired, inducible promoters are the regulatory element of choice. The ability to selectively induce the expression of specific genes allows for the manipulation of development and function not only at the cellular level, but also at the system and organismal level. Generally, a specific nucleotide sequence known as a response element is located in the 5' regulatory region of a target gene that is activated by the stimulus. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Where expression in specific tissues or organs is desired, tissue-preferred promoters are used; these promoters can preferentially drive expression in specific tissues or organs. Examples of promoters under developmental control include promoters that initiate transcription only, or preferentially, in certain tissues, such as leaves, roots, fruit, seeds, or flowers. Exemplary promoters include the anther-specific promoter 5126 (U.S. Pat. Nos. 5,689,049 and 5,689,051), glb-1 promoter, and gamma-zein promoter. See U.S. Pat. No. 5,986,174 for a discussion of methods to identify tissue-preferred transcriptional regulatory elements.

Additional regulatory sequences upstream and/or downstream from the core promoter sequence can be included in expression cassettes of transformation vectors to bring about varying levels of expression of heterologous nucleotide sequences in a transgenic plant.

Reproductive Biology

Control of pollen fertility is essential in hybrid crop production. In hybrid maize production, control of pollen fertility is typically accomplished by physically removing the male inflorescence, or tassel, prior to pollen shed. Manual detasseling is highly labor-intensive. Although mechanical detasseling is less labor-intensive than manual detasseling, mechanical detasseling is less reliable; it requires subsequent examination of the crop and may require remedial manual detasseling. Both methods of detasseling cause a reduction of yield.

Pollen fertility can also be controlled by applying a chemical composition to the plant or soil to prevent pollen production in female plants. See, for example, Ackrnann et al., U.S. Pat. No. 4,801,326. According to this method, hybrid seeds are produced by the fertilization of the treated female plants with pollen from non-treated plants. However, the chemical approach is labor-intensive and presents potential problems with the toxicity of chemicals introduced into the environment.

Another approach to the control of fertility is based upon the use of a cytoplasmic gene(s) for male sterility. See, for example, Patterson, U.S. Pat. No. 3,861,079. The problem with this approach, however, is that the expression of certain cytoplasmic male sterility genes is accompanied by increased susceptibility to fungal pathogens. For example, extensive use of one cytotype, cmsT, led to an epiphytic outbreak of Southern Corn Leaf Blight in the early 1970's. Although additional cms cytotypes have become available, their use has not become widespread due to the concern over possible susceptibility to the Southern Corn Leaf Blight pathogen, or to other, as yet unknown, pathogens.

One type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system.

Other attempts have been made to improve on these methods to control fertility. For example, see EPO 0329308 and WO 90/08828, which describe an antisense system in which a gene critical to fertility is identified and an antisense construct to that gene is used to generate sterility. U.S. Pat. No. 5,426,041 describes a method of transforming plants to produce a gene product which interferes with pollen formation and/or function.

In summary, a functional promoter which can be induced by exogenous application of an auxin and which results in preferential expression in specific tissues or organs is of interest. A need continues to exist for novel methods of controlling fertility in maize plants. Combination of the inducible, tissue-preferred promoter with a gene to overcome male sterility would be useful, particularly in hybridization of maize.

Transformation

Current methods for genetic engineering in maize require a specific cell type as the recipient of new DNA. These cells are found in relatively undifferentiated, rapidly-growing callus cells, or on the scutellar surface of the immature embryo (which gives rise to callus). Irrespective of the delivery method currently used, DNA is introduced into thousands of cells, yet stably-transformed cells are recovered at frequencies of $10^{-5}$ relative to transiently-expressing cells. Exacerbating this problem, the trauma that accompanies DNA introduction directs recipient cells into cell cycle arrest, and evidence suggests that many of these cells are directed into apoptosis or programmed cell death. (Bowen et al., *Third International Congress of the International Society for Plant Molecular Biology*, 1991, Abstract 1093). Therefore it would be desirable to provide improved methods capable of increasing transformation efficiency.

While significant advances in plant transformation have been made over the last few years, in major crop plants, such as maize and soybeans, serious genotype limitations still exist. Transformation of model genotypes is efficient, but many elite genotypes fail to produce a favorable culture response, and the process of introgressing transgenes into production inbreds is laborious, expensive and time-consuming. One approach to improving recovery of transformants from culture is through expression of polynucleotides which may enhance tissue culture response, induce somatic embryogenesis, induce apomixis, increase transformation efficiency and/or increase recovery of regenerated plants. This would include, for example, expression in transformed cells of a LEC1 (leafy cotyledon 1) polynucleotide (U.S. patent application Ser. No. 09/435,054 and WO 00/28058, hereby incorporated by reference). However, a preferred promoter is needed to optimize improvements in transformation efficiency such as that conferred by LEC1.

SUMMARY OF THE INVENTION

Generally, it is an object of the present invention to provide nucleic acids and proteins relating to an auxin-induced polynucleotide, ZmAxig1, including transcription regulatory elements of said polynucleotide. It is an object of the present invention to provide transgenic plants comprising the nucleic acids of the present invention, and methods for modulating, in a transgenic plant, the expression of the nucleic acids of the present invention.

Therefore, in one aspect the present invention relates to an isolated nucleic acid comprising a member selected from the group consisting of (a) a polynucleotide having a specified sequence identity to a polynucleotide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In other aspects the present invention relates to: 1) recombinant expression cassettes comprising a nucleic acid of the present invention operably linked to a gene of interest, 2) a host cell into which has been introduced the recombinant expression cassette, and 3) a transgenic plant comprising the recombinant expression cassette. The host cell and plant are optionally a maize cell or maize plant, respectively.

It is also an object of the present invention to provide a novel nucleotide sequence for modulating gene expression in a plant.

It is a further object of the present invention to provide an isolated promoter capable of driving expression in response to exogenous auxin. The promoter of the present invention can be used to drive expression not only of its native coding sequence, but also of heterologous nucleotide sequences.

It is a further object of the present invention to provide a method for creating useful changes in the phenotype of a transformed plant.

It is a further object of the present invention to provide a method for producing a novel product in a transformed plant.

It is a further object of the present invention to provide a method for producing a novel function or restoring an interrupted function in a transformed plant.

It is a further object of the present invention to provide a method for improving transformation efficiency.

Therefore, in one aspect, the present invention relates to an isolated nucleic acid comprising a member selected from the group consisting of:

a) nucleic acids driving expression of the polynucleotide encoding ZmAxig1;

b) nucleic acids comprising a functional variant or fragment of the sequence set forth in SEQ ID NO: 3, 4, or 16;

c) the nucleic acid set forth in SEQ ID NO: 3, 4, or 16;

d) the nucleic acids deposited with the American Type Culture Collection on Aug. 29, 2000, and designated as PTA-2426 and PTA-2427;

e) nucleic acids that hybridize to any one of a), b), c) or d), under stringent conditions, wherein stringent conditions include: hybridization at 42° C. in a solution of 50% (w/v) formamide, 6×SSC, 0.5% SDS, 100 µg/ml salmon sperm DNA, washed with 0.5% SDS and 0.1×SSC at about 65° C. for about 30 minutes and repeated; and f) nucleic acids having at least 75% sequence identity to SEQ ID NO.: 3, 4, or 16 wherein the % sequence identity is based on the entire sequence and is determined by GAP analysis under default parameters.

g) Nucleic acids isolated from the 5' regulatory region of a polynucleotide having at least 75% identity to the ZmAxig1 maize coding region.

h) In other aspects, the present invention relates to expression cassettes comprising the promoter operably linked to a nucleotide sequence, vectors containing the expression cassette, and plants stably transformed with at least one such expression cassette.

In a further aspect, the present invention relates to a method for modulating expression in a stably transformed plant, comprising the steps of (a) transforming a plant cell with an expression cassette comprising the promoter of the present invention operably linked to at least one nucleotide sequence; (b) growing the plant cell under appropriate growing conditions and (c) regenerating a stably transformed plant from the plant cell wherein the linked nucleotide sequence is expressed upon induction of said promoter with an auxin.

In a further aspect, the present invention relates to a method for modulating gene expression in tissue culture, comprising the steps of (a) transforming a plant cell with an expression cassette comprising the promoter of the present invention operably linked to at least one nucleotide sequence; and (b) growing the plant cell under appropriate growing conditions wherein the linked nucleotide sequence is expressed upon induction of said promoter with an auxin.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants is listed in Table 4 of Murray et al., supra. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.).

As used herein, "full-length sequence" in reference to a specified polynucleotide or its encoded protein means having the entire amino acid sequence of a native (non-synthetic), endogenous, biologically-active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. A particularly preferred monocotyledonous host cell is a maize host cell.

The term "introduced," in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868; PCT publication No. WO 97/20078; Zhang, J.-H., et al. *Proc. Natl. Acad. Sci. USA* 94:4504–4509 (1997).

Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally-occurring nucleotides (e.g., peptide nucleic acids).

Unless otherwise stated, a "ZmAxig1 nucleic acid" is a nucleic acid of the present invention and means a nucleic acid comprising a polynucleotide of the present invention (a "ZmAxig1 polynucleotide").

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. The term polynucleotide as it is employed herein embraces chemically-, enzymatically- or metabolically-modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms include reference to analogues of naturally occurring amino acids which, when incorporated into a protein, do not alter that protein's antibody reactivity.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue can be identified, isolated, and used with other core promoters.

A "plant promoter" is a promoter capable of initiating transcription in plant cells, whether or not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, anthers, or seeds. Such promoters are referred to as "tissue-preferred". Promoters which initiate transcription only in certain tissue are referred to as "tissue-specific". A "cell-type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, the presence of light, or the presence of a growth regulator such as an auxin. Tissue-specific, tissue-preferred, cell-type-specific, and inducible promoters constitute the class of "non-constitutive" promoters. A "constitutive" promoter is a promoter which is active under most environmental conditions.

The term "ZmAxig1 polypeptide" refers to a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "ZmAxig1 protein" is a protein of the present invention and comprises a ZmAxig1 polypeptide.

As used herein, "recombinant" includes reference to a cell or vector that has been modified by the introduction of a heterologous nucleic acid, or to a cell derived from a cell so modified. Thus, for example, as a result of deliberate human intervention, recombinant cells express genes that are not found in identical form within the native (non-recombinant) form of the cell, or express native genes that are otherwise abnormally expressed, under-expressed or not expressed at all, or exhibit reduced expression of a native gene, relative to a non-recombinant cell. The term "recombinant" as used herein does not encompass the alteration of the cell or vector by naturally-occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein").

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low-stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate-stringency conditions include hybridization in 40 to 45% formamide, 1 M NaCl, 1% SDS at 37° C., and a wash in 0.5× to 1×SSC at 55 to 60° C. Exemplary high-stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. Hybridization and/or wash conditions can be applied for at least 10, 30, 60, 90, 120, or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

As used herein, "transgenic plant" includes reference to a plant which comprises within its genome a heterologous polynucleotide. "Transgenic" is used herein to include any cell, cell line, callus, tissue, plant part or plant, the genotype of which has been altered by the presence of heterologous nucleic acid, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally-occurring events.

By "variants" is intended substantially identical sequences. Naturally-occurring variants can be identified and/or isolated with the use of well-known molecular biology techniques, as, for example, with PCR and hybridization techniques as outlined herein. Other variants, such as those resulting from site-directed mutagenesis, are also encompassed by the compositions of the present invention.

As used herein, "vector" includes reference to a nucleic acid used in introduction of a polynucleotide of the present invention into a host cell. Vectors are often replicons. Expression vectors permit transcription of a nucleic acid inserted therein.

Methods of alignment of sequences for comparison are well known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, CABIOS 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs can be used for database similarity searches. See, *Current Protocols in Molecular Biology*, Chapter 19, Ausubel, et al., Eds., Greene Publishing and Wiley-Interscience, New York (1995); Altschul et al., *J. Mol. Biol.*, 215:403–410 (1990); Henikoff & Henikoff (1989) *Proc. Natl. Acad. Sci. USA* 89:10915; Karlin & Altschul, *Proc. Nat'l. Acad. Sci. USA* 90:5873–5877 (1993); Wooten and Federhen, *Comput. Chem.*, 17:149–163 (1993); Clayerie and States, *Comput. Chem.*, 17:191–201 (1993); and, Altschul et al., *Nucleic Acids Res.* 25:3389–3402 (1997). Software for performing BLAST analyses is publicly available, e.g., through the National Center for Biotechnology Information, U.S. National Library of Medicine, 8600 Rockville Pike, Bethesda, Md. 20894.

GAP (Global Alignment Program) can also be used to compare a polynucleotide or polypeptide of the present invention with a reference sequence. Unless otherwise stated, nucleotide and protein identity/similarity values provided herein are calculated using GAP (GCG Version 10) under default values. GAP uses the algorithm of Needleman and Wunsch (*J. Mol. Biol.* 48: 443–453, 1970) to find the alignment of two complete sequences that maximizes the number of matches and minimizes the number of gaps.

Multiple alignment of the sequences can be performed using the CLUSTAL method of alignment (Higgins and Sharp (1989) *CABIOS.* 5:151–153).

As used herein, "sequence identity" or "identity" in the context of two nucleic acid or polypeptide sequences includes reference to the residues in the two sequences which are the same when aligned for maximum correspondence over a specified comparison window.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

BRIEF DESCRIPTION OF THE DRAWINGS

FIG. 2 is a GAP comparison of DNA sequences of cloned band w0h051.7 (SEQ ID No. 13) and Pioneer EST CJLPI81 (SEQ ID No. 12).

FIG. 5 is a comparison of the amino acid sequences of the putative ZmAxig1 protein product and PS-IAA4/5.

FIG. 9 is a GAP comparison of the full-length ZmAxig1 sequence (Sequence ID No. 5) and the CZAAL47 sequence (Sequence ID No. 1).

FIG. 10 provides sequence names corresponding to SEQ ID NOs.

FIG. 11 shows effect of Lec1 constructs on transformation efficiency.

DETAILED DESCRIPTION OF THE INVENTION

Overview

Figure 1:
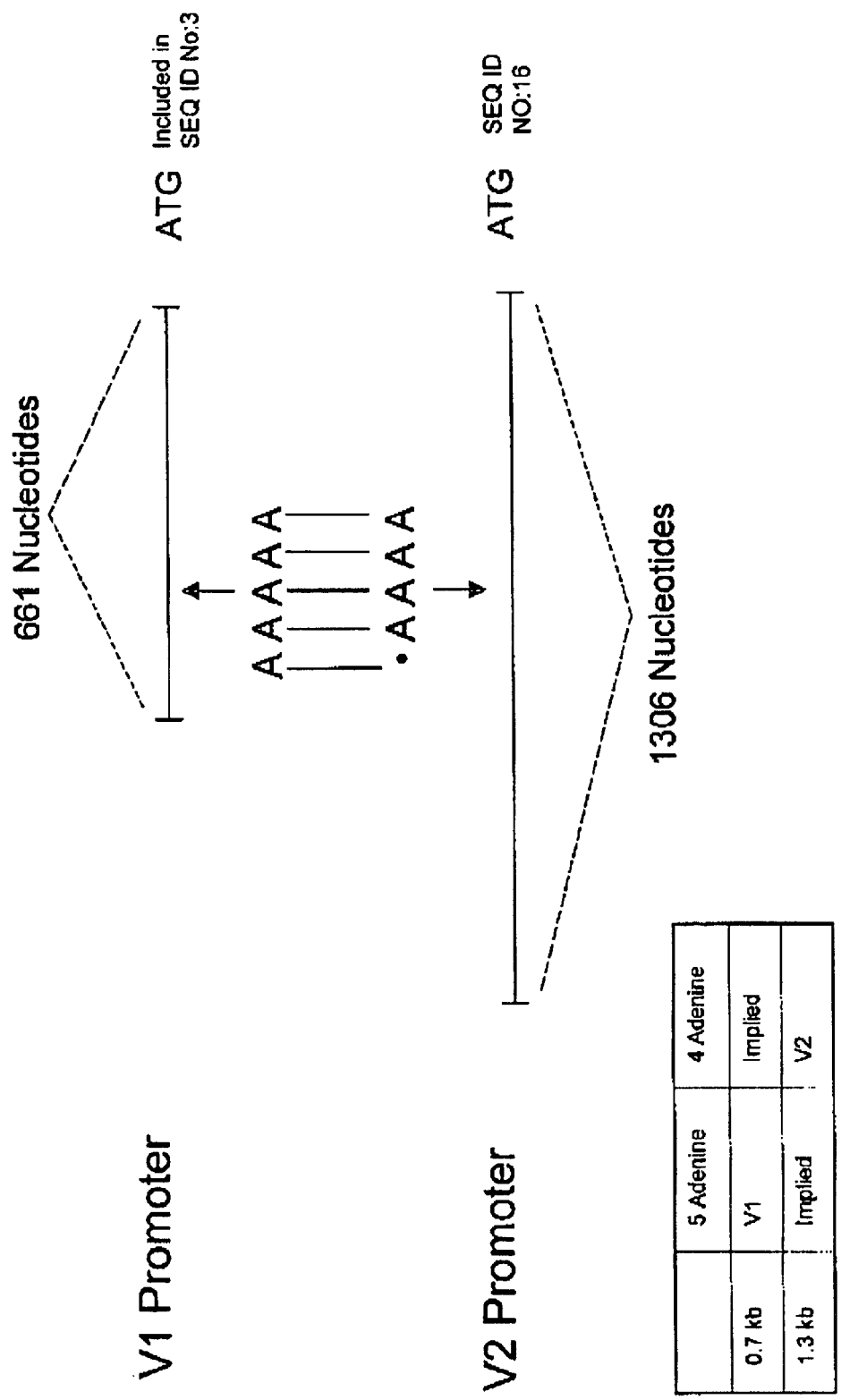
FIG. 1 shows the average gel trace of digested cDNA fragments from dicamba-treated anthers (upper panel) or non-treated anthers (lower panel). The peak showing expression level for w0h051.7 (SEQ ID No. 13) is marked with a vertical line. The y axis is in arbitrary fluorescence units, whereas the x axis is in base pairs of nucleotides.

In accordance with the invention, a nucleotide sequence is provided that preferentially initiates transcription in response to presence of an auxin. The sequences of the invention comprise transcription initiation regions associated with hormone responsiveness and preferential expression in male reproductive tissues and/or in callus tissue. Thus, certain compositions of the present invention comprise a novel nucleotide sequence for a plant promoter, more particularly an auxin-responsive, tapetum-preferred or callus-preferred promoter for the gene ZmAxig1. Said novel nucleotide sequence has been found to comprise two copies of the sequence TGTCNC, recognized by those of skill in the art as a putative auxin response element which may function globally within plant genomes and could potentially be coupled with other expression factors to provide temporal, tissue, and/or developmental specificity of hormone-induced expression for a particular gene.

The promoter of the present invention can be obtained from the flanking region 5' of and including its respective transcription initiation site. Methods for isolation of promoter regions are well known in the art. One method is described in U.S. patent application Ser. No. 09/387,720 filed Aug. 30, 1999. A sequence for the promoter region including the 5' untranslated region is set forth in each of SEQ ID NOS: 3, 4, and 16.

The isolated promoter sequence of the present invention can be modified to provide for a range of induced and/or uninduced expression levels of the heterologous nucleotide sequence. Less than the entire promoter region can be utilized and the ability to drive preferential expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

Smaller fragments may yet contain the regulatory properties of the promoter, and deletion analysis is one method of identifying essential regions. Deletion analysis can occur from both the 5' and 3' ends of the regulatory region. Fragments can be obtained by linker-scanning mutagenesis, mutagenesis using the polymerase chain reaction, and the like. (See, *Directed Mutagenesis: A Practical Approach IRL Press* (1991)). The 3' deletions can identify the 3' end and delineate the essential region so that this region may then be operably linked to a core promoter of choice. Once the essential region is identified, transcription of an exogenous gene may be controlled by the essential region plus a core promoter. The core promoter can be any one of known core promoters such as the Cauliflower Mosaic Virus 35S or 19S promoter (U.S. Pat. No. 5,352,605), ubiquitin promoter (U.S. Pat. No. 5,510,474), the IN2 core promoter (U.S. Pat. No. 5,364,780), or a Figwort Mosaic Virus promoter (Gruber, et al. "Vectors for Plant Transformation" *Methods in Plant Molecular Biology and Biotechnology* Glick et al. eds, CRC Press pp.89–119 (1993)).

The promoter region of the invention may be isolated from any plant, including, but not limited to, maize (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), oats (*Avena sativa*), and barley (*Hordeum vulgare*). Preferably, plants include maize, soybean, sunflower, safflower, canola, wheat, barley, rye, alfalfa, and sorghum.

Promoter sequences may be isolated according to well-known techniques based on homology to a promoter sequence set forth herein, or based on proximity to polynucleotides homologous to the coding region of ZmAxig1. In these techniques, all or part of the known sequence may be used as a probe which selectively hybridizes to certain sequences present in a population of cloned genomic DNA fragments (i.e. genomic libraries) from a chosen organism. Probes may also be used to isolate nucleic acid fragments of interest from a population of nucleic acids not existing as part of a library. Methods are readily available in the art for the hybridization of nucleic acid sequences. Sequence comparison software, as described supra, may also be utilized to identify homologous polynucleotides.

In general, sequences that correspond to the promoter sequence of the present invention and hybridize to the promoter sequence disclosed herein will be at least 50% homologous, 70% homologous, and even 85% homologous or more with the disclosed sequence. That is, the sequence similarity between probe and target may range, sharing at least about 50%, 55%, 60%, 65%, 70%, 75%, and even about 80%, 85%, 90%, 95%, 99%, or 100% sequence similarity.

Preferred hybridization conditions for the promoter sequence of the invention include hybridization at 42° C. in 50% (w/v) formamide, 6×SSC, 0.5% SDS, 100 μg/ml salmon sperm DNA. Exemplary low stringency conditions include a wash at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 0.1×SSC, 0.5% (w/v) SDS, at about 65° C. for about 30 minutes, and repeating. Sequences that correspond to the promoter of the present invention may be obtained using all the above conditions. For purposes of defining the invention, the high stringency conditions are used.

Further, the nucleotide sequence for the promoter of the invention, the ZmAxig1 promoter, as well as fragments and variants thereof, can be provided in expression cassettes along with heterologous nucleotide sequences for expression in the plant or plant tissue culture of interest. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response. To improve transformation frequency, the expression cassette may include polynucleotides enhancing tissue culture response, such as LEC1 polynucleotides (see WO 00/28058). The expression cassette will also include, at the 3' terminus of the heterologous nucleotide sequence of interest, a transcriptional and translational termination region functional in plants. The termination region can be native to the promoter nucleotide sequence of the present invention, can be native to the DNA sequence of interest, or can be derived from another source. Convenient termination regions are available from the Ti-plasmid of *A. tumefaciens*, such as the octopine synthase and nopaline synthase termination regions. See also, Guerineau et al., *Mol. Gen. Genet.* 262:141–144 (1991); Proudfoot, *Cell* 64:671–674 (1991); Sanfacon et al., *Genes Dev.* 5:141–149 (1991); Mogen et al., *Plant Cell* 2:1261–1272 (1990); Munroe et al., *Gene* 91:151–158 (1990); Ballas et al., *Nucleic Acids Res.* 17:7891–7903 (1989); Joshi et al., *Nucleic Acid Res.* 15:9627–9639 (1987).

Examples of other nucleotide sequences which can be used with the ZmAxig1 promoter or variants include complementary nucleotidic units such as antisense molecules (callase antisense RNA, barnase antisense RNA and chalcone synthase antisense RNA, Ms45 antisense RNA), ribozymes and external guide sequences, an aptamer or single stranded nucleotides. Also, the heterologous nucleotide sequence may encode rol B, DAM methylase, avidin, or certain cytotoxins; may encode proteins involved in the biosynthesis of auxins or diphtheria toxin; or may be selected from a prokaryotic regulatory system. By way of example, Mariani, et al., *Nature*: Vol. 347; pp. 737; (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Quaas, et al., *Eur. J. Biochem.* Vol. 173: pp. 617 (1988), describe the chemical synthesis of the RNase-T1, while the nucleotide sequence of the barnase gene is disclosed in Hartley, *J. Molec. Biol.*; Vol. 202: pp. 913 (1988). The rolB gene of *Agrobacterium rhizogenes* codes for an enzyme that interferes with auxin metabolism by catalyzing the release of free indoles from indoxyl-β-glucosides. Estruch, et al., *EMBO J.* Vol. 11: pp. 3125 (1991) and Spena, et al., *Theor. Appl. Genet.*: Vol. 84: pp. 520 (1992), have shown that the anther-specific expression of the rolB gene in tobacco resulted in plants having shriveled anthers in which pollen production was severely decreased and shown the rolB gene is an example of a gene that is useful for the control of pollen production. Slightom, et al., *J. Biol. Chem.* Vol. 261: pp. 108 (1985), disclose the nucleotide sequence of the rolB gene. DNA molecules encoding the diphtheria toxin gene can be obtained from the American Type Culture Collection (Rockville, Md.), ATCC No. 39359 or ATCC No. 67011 and see Fabijanski, et al., E.P. Appl. No. 90902754.2, "Molecular Methods of Hybrid Seed Production" for examples and methods of use. The DAM methylase gene is used to cause sterility in the methods discussed at U.S. Pat. No. 5,689,049 and PCT/US95/15229; Cigan, A. M. and Albertsen, M. C., "Reversible Nuclear Genetic System for Male Sterility in Transgenic Plants". Also see discussion of use of the avidin gene to cause sterility at U.S. Pat. No. 5,962,769, "Induction of Male Sterility in Plants by Expression of High Levels of Avidin," Albertsen, M., and Howard, J.

The present invention also provides, among other things, compositions and methods for modulating (i.e., increasing or decreasing), in plants or plant tissue cultures, the levels of polynucleotides and polypeptides of interest. In particular, the polynucleotides of the present invention can be expressed temporally or spatially, e.g., at developmental stages, in tissues, and/or in quantities, which are uncharacteristic of non-recombinantly engineered plants or plant cells. Thus, the present invention provides utility in such exemplary applications as modifying plant response to auxins, including changes in development of vascular tissues, formation of lateral and adventitious roots, control of apical dominance, and tropic responses. In particular, tissue-preferred expression in response to auxin, as provided by the present invention, could be useful in such exemplary applications as restoration of fertility in genetically sterile maize plants.

In addition, it may be advantageous to restrict expression of a given trait in certain or all tissues when such expression is not required or not desirable. The tissue-preferred expression exemplified by the present invention provides utility in designing such systems to restrict gene expression. For example, a promoter having tissue-preferred or temporal-specific expression could be combined with an antisense construct for the gene of interest, reducing or eliminating expression of the gene of interest in particular plant tissues and/or at particular develomental stages.

Additionally, the anther-preferred nature of the ZmAxig1 promoter allows design of systems, such as antisense, to downregulate gene expression during microspore development. That is, a construct combining the auxin-induced, anther-preferred ZmAxig1 promoter with a structural gene in antisense orientation would provide inducible, tissue-preferred restriction of expression of, for example, otherwise-constitutively expressed native genes or transgenes. Restriction of expression in microspore development would be useful in alleviating certain environmental concerns associated with transgenic plants.

Further, the ZmAxig1 promoter could be used to drive genes which confer a growth advantage in culture or induce embryogenesis of cultured cells.

The expression cassette can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. *Proc. Nat. Acad. Sci. USA* 86:6126–6130 (1989); potyvirus leaders, for example, TEV leader (Tobacco Etch Virus), Allison et al.; MDMV leader (Maize Dwarf Mosaic Virus), *Virology* 154:9–20 (1986); human immunoglobulin heavy-chain binding protein (BiP), Macejak et al., *Nature* 353:90–94 (1991); untranslated leader from the coat protein mRNA of alfalfa mosaic virus (AMV RNA 4), Jobling et al. *Nature* 325:622–625 (1987); Tobacco mosaic virus leader (TMV), Gallie et al. (1989) *Molecular Biology of RNA*, pages 237–256; and maize chlorotic mottle virus leader (MCMV) Lommel et al., *Virology* 81:382–385 (1991). See also Della-Cioppa et al., *Plant Physiology* 84:965–968 (1987). The cassette can also contain sequences that enhance translation and/or mRNA stability such as introns.

In those instances where it is desirable to have the expressed product of the heterologous nucleotide sequence directed to a particular organelle, particularly the plastid, amyloplast, or endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731–3738 (1985)). Use of transit peptides is well known (e.g., see U.S. Pat. Nos. 5,717,084; 5,728,925).

In preparing the expression cassette, the various DNA fragments can be manipulated so as to provide for the DNA sequences in the proper orientation and, as appropriate, in the proper reading frame. Toward this end, adapters or linkers can be employed to join the DNA fragments, or other manipulations can be involved to provide for convenient restriction sites, removal of superfluous DNA, removal of restriction sites, and the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook, et al. (supra).

The transformation vector, comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

The invention also includes vectors comprising the ZmAxig1 gene. A vector is prepared comprising the ZmAxig1 coding sequence, a promoter which will drive expression of the gene in the plant, and a terminator region. As noted, the promoter in the construct may be the native promoter or a substituted promoter which will provide expression in the plant. Selection of the promoter will depend upon the intended use of the gene. There may be other components of the vector, chosen depending upon intended use, such as selectable markers, targeting or regulatory sequences, stabilizing or leader sequences, etc. See, for example, Gruber, et al., supra. The selection of an appropriate expression vector will depend upon the host and the method of introducing the expression vector into the host. The expression cassette will also include, at the 3' terminus of the heterologous nucleotide sequence of interest, a transcriptional and translational termination region functional in plants. The termination region can be native to the promoter nucleotide sequence of the present invention, can be native to the DNA sequence of interest, or can be derived from another source. Convenient termination regions are available from the Ti-plasmid of *A. tumefaciens*, such as the octopine synthase and nopaline synthase termination regions. See also, Guerineau et al., *Mol. Gen. Genet.* 262:141–144 (1991); Proudfoot, *Cell* 64:671–674 (1991); Sanfacon et al., *Genes Dev.* 5:141–149 (1991); Mogen et al., *Plant Cell* 2:1261–1272 (1990); Munroe et al., *Gene* 91:151–158 (1990); Ballas et al., *Nucleic Acids Res.* 17:7891–7903 (1989); Joshi et al., *Nucleic Acid Res.* 15:9627–9639 (1987).

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. *Mol. Cell. Biol.* 7:725–737 (1987); Goff et al. *EMBO J.* 9:2517–2522 (1990); Kain et al. *BioTechniques* 19:650–655 (1995); and Chiu et al. *Current Biology* 6:325–330 (1996).

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. *EMBO J.* 2:987–992(1983); methotrexate, Herrera Estrella et al. *Nature* 303:209–213(1983); Meijer et al. *Plant Mol. Biol.* 16:807–820 (1991); hygromycin, Waldron et al. *Plant Mol. Biol.* 5:103–108 (1985); Zhijian et al. *Plant Science* 108:219–227 (1995); streptomycin, Jones et al. *Mol. Gen. Genet.* 210:86–91(1987); spectinomycin, Bretagne-Sagnard et al. *Transgenic Res.* 5:131–137 (1996); bleomycin, Hille et al. *Plant Mol. Biol.* 7:171–176 (1990); sulfonamide, Guerineau et al. *Plant Mol. Biol.* 15:127–136(1990); bromoxynil, Stalker et al. *Science* 242:419–423 (1988); glyphosate, Shaw et al. *Science* 233:478–481(1986); phosphinothricin, DeBlock et al. *EMBO J.* 6:2513–2518 (1987).

The present invention also provides isolated nucleic acids comprising polynucleotides of sufficient length and complementarity to a gene of the present invention to use as probes or amplification primers in the detection, quantitation, or isolation of gene transcripts. For example, isolated nucleic acids of the present invention can be used as probes in detecting differences in mRNA levels in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site-directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The isolated nucleic acids and polypeptides of the present invention can be used over a broad range of plant types, particularly monocots such as the species of the family Gramineae including *Hordeum*, *Secale*, *Triticum*, *Sorghum* (e.g., *S. bicolor*) and *Zea* (e.g., *Z. mays*). The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa,*

*Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Glycine, Pisum, Phaseolus, Lolium, Oryza,* and *Avena.*
Nucleic Acids Unless otherwise stated, the polynucleotide sequences identified in FIG. 10 represent polynucleotides of the present invention. A nucleic acid of the present invention comprises a polynucleotide of the present invention.

The present invention provides, among other things, isolated nucleic acids of RNA, DNA, and analogs and/or chimeras thereof, comprising a polynucleotide of the present invention.

A polynucleotide of the present invention is inclusive of:

(a) the exemplary polynucleotides of FIG. 10;

(b) a polynucleotide which is the product of amplification from a *Zea mays* nucleic acid library using primer pairs which selectively hybridize under stringent conditions to loci within a polynucleotide of the present invention;

(c) an isolated polynucleotide which selectively hybridizes to a polynucleotide of (a);

(d) an isolated polynucleotide having a specified sequence identity with a polynucleotide of (a), (b), or (c);

(e) complementary sequences of polynucleotides of (a), (b), or (d).

A. Polynucleotides of FIG. 10

As indicated in (a), above, the present invention provides isolated nucleic acids comprising a polynucleotide of the present invention. In addition, each variant nucleic acid which encodes a polypeptide of the present invention is implicit in each described polypeptide sequence and is within the scope of the present invention.

SEQ ID Nos. 3, 4, and 16 are representative of the ZmAxig1 promoter region.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a *Zea mays* nucleic acid library. Nucleic acid amplification conditions for each of the variety of amplification methods are well known to those of ordinary skill in the art. The plant nucleic acids can be from a monocot such as a cereal crop. Exemplary cereals include maize, sorghum, wheat, and rice. The plant nucleic acids can also be from a dicot such as soybean, alfalfa, or canola. *Zea mays* lines B73, A632, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. Rapidly-growing tissues or rapidly-dividing cells are preferred for use as an mRNA source for construction of a cDNA library. An especially-preferred cDNA library is constructed from anther tissue of *Zea mays* plants treated with two daily soil drenches of 12 $\mu$l dicamba formulation (Banvel®, 48.2% active ingredient dicamba) in 450 ml water. cDNA libraries can be normalized to increase the representation of relatively rare cDNAs. In optional embodiments, the cDNA library is constructed using an enriched full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995).

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention such that a single contiguous nucleic acid can be formed under the desired amplification conditions.

In optional embodiments, the primers will be constructed so that they selectively hybridize under stringent conditions to a sequence (or its complement) within the target nucleic acid which comprises the 3' terminal coding region or 5' terminal coding region of a polynucleotide of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Preferred primers comprise those listed as SEQ ID NOS. 6, 7, 8, 9, 10, 14 and 15.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more epitopes which are specific to a polypeptide of the present invention. Methods for protein synthesis from PCR-derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, *Techniques* 1:165 (1989).

C. Polynucleotides Which Selectively Hybridize to a Polynucleotide of (A) or (B)

As indicated in (c), above, the present invention provides isolated polynucleotides which selectively hybridize to a polynucleotide of (A) or (B) above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library.

D. Polynucleotides Having a Specific Sequence Identity with the Polynucleotides of (A), (B) or (C)

As indicated in (d), above, the present invention provides isolated polynucleotides having a specified identity at the nucleotide level to a polynucleotide as disclosed above in sections (A), (B), or (C). Identity can be calculated using, for example, the BLAST, CLUSTALW, or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least about 50%, 55%, 60%, 65%, 70%, 75%, and even about 80%, 85%, 90%, 95%, 99%, or 100%.

Optionally, the polynucleotides of the present invention will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the second polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. In addition to direct chemical synthetic methods for generating peptide libraries, several recombinant DNA methods have been described. See, for example, PCT patent publication Nos. 91/17271, 91/18980, 91/19818, 93/08278, 92/05258, 92/14843, and 97/20078 and U.S. Pat. Nos. 5,658,754 and 5,643,768.

E. Polynucleotides Complementary to the Polynucleotides of (A), (B), or (D)

As indicated in (e), above, the present invention provides isolated nucleic acids comprising polynucleotides complementary to the polynucleotides of sections A, B, or D, above.

Construction of Nucleic Acids

The isolated nucleic acids of the present invention can be made using (a) standard recombinant methods, (b) synthetic techniques, or (c) combinations thereof. In some embodiments, the polynucleotides of the present invention will be cloned, amplified, or otherwise constructed from a monocot. In preferred embodiments the monocot is *Zea mays*. Such techniques are well known to those of skill in the art; for example, see Sambrook, et al., *Molecular Cloning: A Laboratory Manual*, 2nd Ed., Cold Spring Harbor Laboratory Vols. 1–3 (1989); Methods in Enzymology, Vol. 152: *Guide to Molecular Cloning Techniques*, Berger and Kimmel, Eds., San Diego: Academic Press, Inc. (1987); *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

The present invention further provides recombinant expression cassettes comprising a nucleic acid of the present invention. A recombinant expression cassette will typically comprise a polynucleotide of the present invention operably linked to transcriptional initiation regulatory sequences which will direct the transcription of the polynucleotide in the intended host cell, such as tissues of a transformed plant.

In some embodiments, isolated nucleic acids which serve as promoter or enhancer elements can be introduced in the appropriate position (generally upstream) of a non-heterologous form of a polynucleotide of the present invention so as to up- or down-regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter, functional in a plant cell, operably linked to a polynucleotide of the present invention. Promoters useful in these embodiments include the endogenous promoters driving expression of a polypeptide of the present invention.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci.* (USA) 85: 8805–8809 (1988); and Hiatt et al., U.S. Pat. No. 4,801,340.

Transfection/Transformation of Cells

The method of transformation/transfection is not critical to the instant invention; various methods of transformation or transfection are currently available. Thus, any method which provides for effective transformation/transfection may be employed. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, *Bio/Technology* 10:268 (1992); and Weising et al., *Ann. Rev. Genet.* 22: 421–477 (1988). For example, the DNA construct may be introduced into the genomic DNA of the plant cell using techniques such as microprojectile-mediated delivery, Klein et al., *Nature* 327: 70–73 (1987); electroporation, Fromm et al., *Proc. Natl. Acad. Sci.* 82: 5824 (1985); polyethylene glycol (PEG) precipitation, Paszkowski et al., *EMBO J.* 3: 2717–2722 (1984); direct gene transfer WO 85/01856 and EP No. 0 275 069; in vitro protoplast transformation U.S. Pat. No. 4,684,611; and microinjection of plant cell protoplasts or embryogenic callus. Crossway, *Mol. Gen. Genetics* 202:179–185 (1985). Co-cultivation of plant tissue with *Agrobacterium tumefaciens* is another option, where the DNA constructs are placed into a binary vector system. See e.g., U.S. Pat. No. 5,591, 616; Ishida et al., "High Efficiency Transformation of Maize (*Zea mays* L.) mediated by *Agrobacterium tumefaciens*"

*Nature Biotechnology* 14:745–750 (1996). The virulence functions of the *Agrobacterium tumefaciens* host will direct the insertion of the construct into the plant cell DNA when the cell is infected by the bacteria. See, for example Horsch et al., *Science* 233: 496–498 (1984), and Fraley et al., *Proc. Natl. Acad. Sci.* 80: 4803 (1983).

Standard methods for transformation of canola are described at Moloney et al. "High Efficiency Transformation of *Brassica napus* using Agrobacterium Vectors" *Plant Cell Reports* 8:238–242 (1989). Corn transformation is described by Fromm et al, *Bio/Technology* 8:833 (1990) and Gordon-Kamm et al, supra. Agrobacterium is primarily used in dicots, but certain monocots such as maize can be transformed by Agrobacterium. See supra and U.S. Pat. No. 5,550,318. Rice transformation is described by Hiei et al., "Efficient Transformation of Rice (*Oryza sativs* L.) Mediated by Agrobacterium and Sequence Analysis of the Boundaries of the T-DNA" *The Plant Journal* 6(2): 271–282 (1994, Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. Sorghum transformation is described at Casas et al, supra and sorghum by Wan et al, *Plant Physiol.* 104:37 (1994). Soybean transformation is described in a number of publications, including U.S. Pat. No. 5,015,580. As newer methods are available to transform crops or other host cells they may be directly applied.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize see, Gordon-Kamm et al., *The Plant Cell*, 2:603–618 (1990). Transgenic plants of the present invention may be fertile or sterile.

Plants cells transformed with a plant expression vector can be regenerated, e.g., from single cells, callus tissue or leaf discs, according to standard plant tissue culture techniques. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227:1229–1231 (1985). Regeneration can also be obtained from plant callus, explants, organs, or parts thereof as described generally in Klee et al., *Ann. Rev. of Plant Phys.* 38: 467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

Parts obtained from the regenerated plant, such as flowers, seeds, leaves, branches, fruit, and the like are included in the invention, provided that these parts comprise cells comprising the isolated nucleic acid of the present invention. Progeny and variants and mutants of the regenerated plants are also included within the scope of the invention, provided that these parts comprise the introduced nucleic acid sequences. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants for altered expression of a polynucleotide of the present invention relative to a control plant (i.e., native, non-transgenic). Back-crossing to a parental plant and out-crossing with a non-transgenic plant are also contemplated.

Induction of expression of a polynucleotide of the present invention may be controlled by exogenous administration of an effective amount of inducing compound. In preferred embodiments, the inducing compound is a natural or synthetic auxin. In preferred embodiments, the polypeptides of the present invention are modulated in monocots, particularly maize.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transgenic plant cell, culturing the transgenic plant cell under transgenic plant cell growing conditions, and allowing, inducing or repressing expression of a polynucleotide of the present invention in the transgenic plant for a time sufficient to modulate concentration and/or the ratios of the polypeptides in the transgenic plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., WO 93/22443. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

Modulating nucleic acid expression temporally and/or in particular tissues can be controlled by employing the appropriate promoter operably linked to a polynucleotide of the present invention in, for example, sense or antisense orientation as discussed in greater detail, supra.

All publications and patent applications mentioned are herein incorporated by reference to the same extent as if each individual publication or patent application were specifically and individually indicated to be incorporated by reference.

Although the present invention is described in some detail by way of illustration and example for purposes of clarity of understanding, it will be obvious that certain changes and modifications may be practiced within the scope of the appended claims.

EXAMPLE 1

RNA Isolation and Profiling

Greenhouse grown maize plants (public inbred A632) were treated with two daily soil drenches of 12 μl dicamba formulation (Banvel®, 48.2% active ingredient dicamba) in 450 ml water. Anthers containing microsporocytes at meiosis II through early uninucleate stages of development were harvested on the third day and frozen. Anthers containing microsporocytes at prophase through early uninucleate stages of development were harvested from non-treated plants. Frozen tissues were ground and total RNA extracted with Tripure™ isolation reagent (Boehringer Mannheim, Indianapolis, Ind.) according to the manufacturer's instructions.

Figure 3:
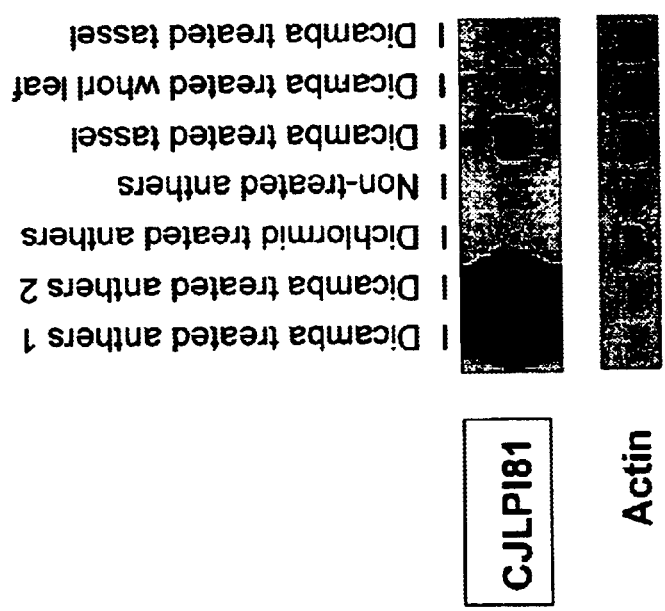
FIG. 3 is a Northern blot probed with CJLPI81 (SEQ ID No. 12) and actin. Lanes contain, from left to right: mRNA from anthers of two different dicamba-treated plants; anthers of a Dichlormid-treated plant; anthers of a non-treated plant; tassel, whorl leaf and tassel of dicamba-treated plants.
Figure 4:
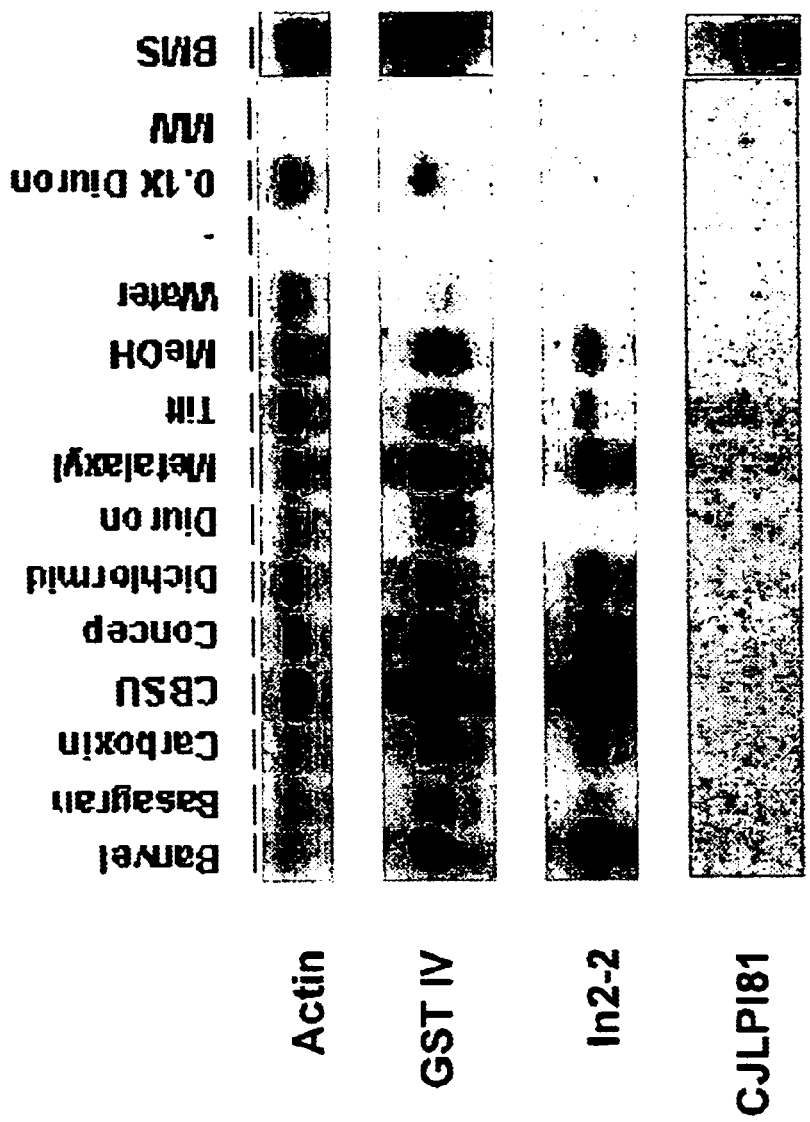
FIG. 4 is a Northern blot probed with actin, GST-IV (Jepson, I., et al. Plant Mol. Biol. 26(6):1855–66 (December 1994)), In2-2 (Hershey, H. P., and T. D. Stoner. Plant Mol. Biol. 17(4):679–90 (October 1991)) and CJLPI81 (SEQ ID No. 12). Lanes contain mRNA from aerial portion of two-week-old seedlings treated with the following agrochemicals, from left to right: Banvel®, Basagran®, Carboxin, CBSU, ConcepIII®, Dichlormid, Diuron, Metalaxyl, Tilt®, methanol carrier, water, 0.1× Diuron. The last lane contains mRNA from cultured BMS cells.

RNA isolated from anthers of three dicamba-treated plants and three non-treated plants was sent to laboratories of CuraGen Corporation (New Haven, Conn.) for quantitative expression profiling. Two peaks in the upper panel of FIG. 1 represent cDNA fragments induced by the treatment and expressed at a level greater than 2.5-fold higher than the control. These two cDNA bands were isolated and sequenced. A 52-bp sequence (SEQ ID No. 13) of each band was also found to appear in two Pioneer EST clones (SEQ ID No. 1 and SEQ ID No. 12); see, for example, FIG. 2. This shared sequence (SEQ ID No. 12) was used to probe northern blots containing mRNA from dicamba-treated plants, non-treated plants, and plants treated with other agrochemicals. The probe hybridized very strongly with mRNA from anthers of dicamba-treated plants. Hybridization was also observed to a lesser degree with mRNA from the tassel or whorl leaf of dicamba-treated plants. (FIG. 3) The same probe also hybridized to mRNA isolated from BMS (Black Mexican Sweet) maize cultured on medium containing the synthetic auxin 2,4-D. The probe did not hybridize to mRNA from the anther or entire aerial portion of untreated plants or plants treated with other agrochemicals, including Dichlormid, CBSU, ConcepIII®, Basagran®, Carboxin, Diuron, Metalaxyl, or Tilt® (FIG. 4).

Sequences identical to SEQ ID. No. 12 and SEQ ID No. 1 have not been found in public databases. The putative gene product shows some similarity to Aux/IAA proteins encoded by a family of auxin-responsive genes isolated from various dicot plants (FIG. 5), and the gene has been named ZmAxig1.

EXAMPLE 2

Expression Analysis

Progeny of transgenic maize plants, hemizygous for the maize anther-preferred promoter 5126 (U.S. Pat. Nos. 5,689,049 and 5,689,051) driving DAM methylase linked with 35S:PAT (p5126:DAM/35S:PAT), were grown in the greenhouse. Expression of p5126:DAM is known to ablate the tapetum prior to the quartet stage of microspore development, which results in male sterile plants.

Figure 6:
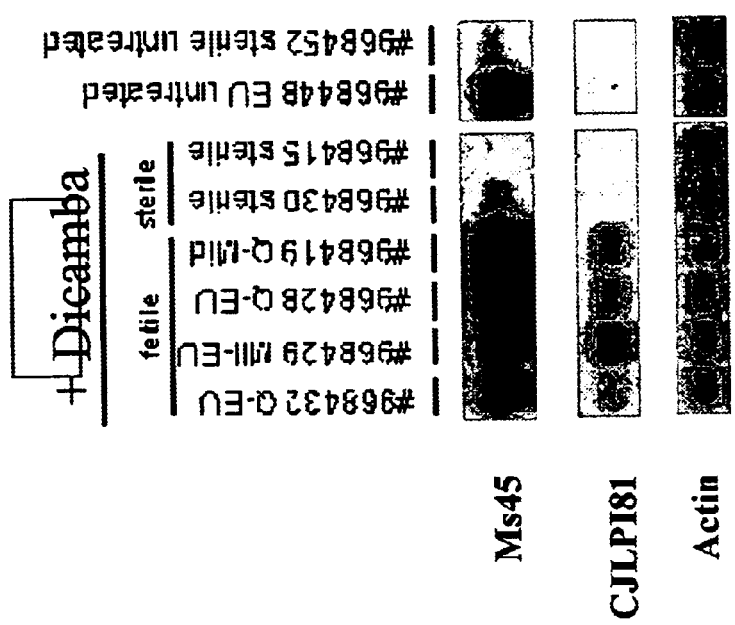
FIG. 6 shows Northern blot analyses of mRNA from anthers from male-fertile or male-sterile 5126:DAM plants treated with dicamba, or not treated.

Plants segregating for male fertile/glufosinate-ammonium susceptible phenotype (wild-type) or for male sterile/glufosinate-ammonium resistant phenotype (p5126:DAM/35S:PAT), were treated with a dicamba soil drench as described above, or were not treated. Quartet/early-uninucleate stage anthers were harvested from these plants and mRNA was isolated with the QuickPrep® Micro mRNA purification kit (Amersham Pharmacia, Piscataway, N.J.) according to the manufacturer's instructions. Northern blot analyses showed that dicamba treatment induced expression of ZmAxig1 only in anthers from wild-type male fertile plants, not in anthers from male sterile plants containing p5126:DAM/35S:PAT (FIG. 6). Additionally, Ms45 expression is detected in anther mRNA from male fertile plants but not in anther mRNA from male sterile p5126:DAM/35S:PAT plants. Ms45 has been shown to be expressed specifically in the tapetum (see U.S. Pat. Nos. 5,478,369 and 6,037,523). These results indicate that dicamba preferentially induces ZmAxig1 expression in the tapetum.

Figure 7:
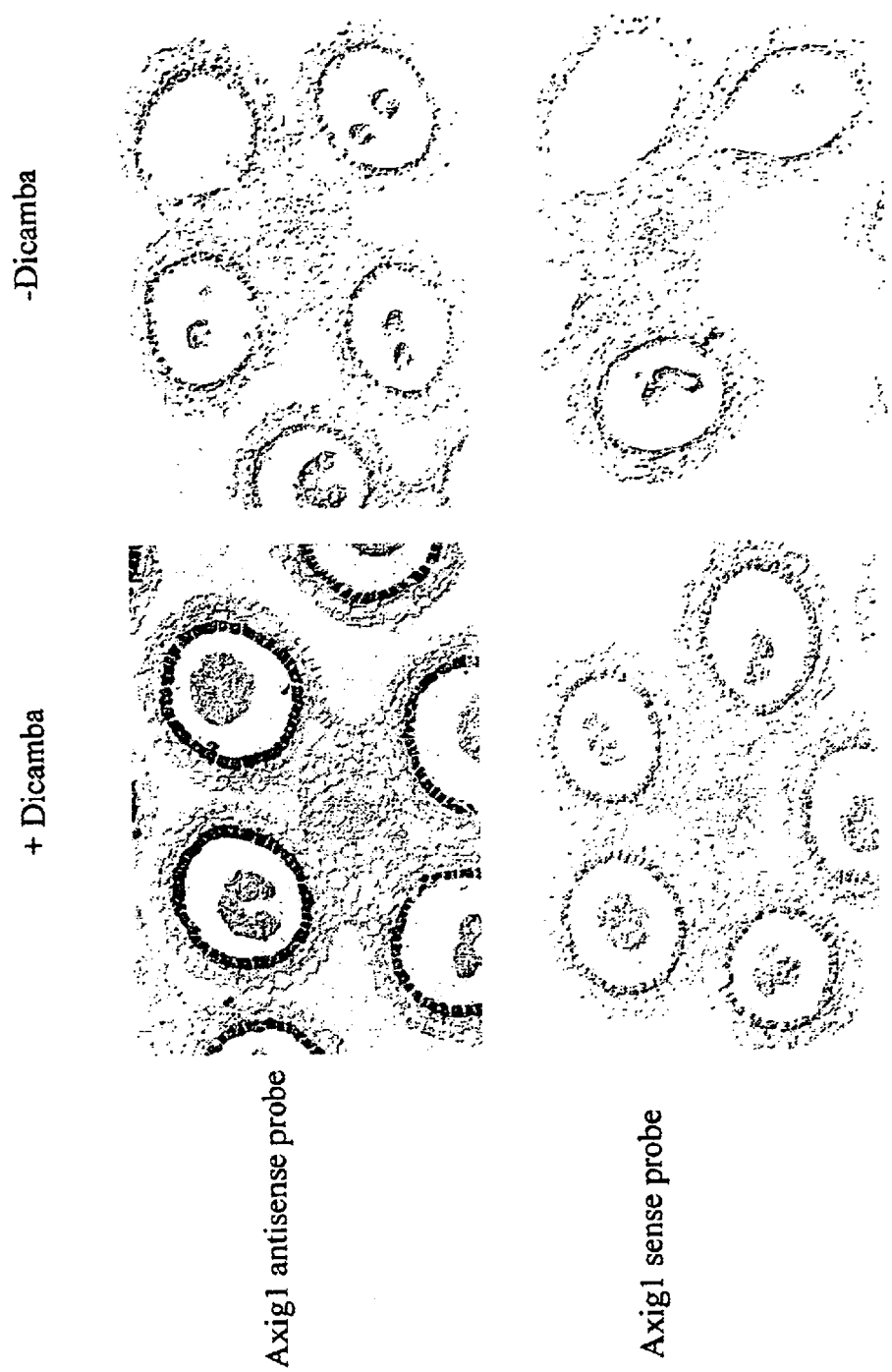
FIG. 7 shows in situ hybridizations with quartet-stage anthers treated with dicamba, or not treated.

Quartet/early-uninucleate stage anthers from dicamba-treated or non-treated plants were harvested and embedded for in situ hybridization or frozen for mRNA isolation as described above. Northern blot analyses showed that ZmAxig1 expression was induced in anthers of dicamba treated plants. ZmAxig1 antisense RNA probe showed strong in situ hybridization to RNA in the tapetum of anthers and microspores from dicamba treated plants and did not show hybridization to anthers from non-treated plants (FIG. 7). The ZmAxig1 sense RNA probe did not show hybridization to anthers from either treatment. Thus, ZmAxig1 transcripts are induced in the tapetum by dicamba treatment.

EXAMPLE 3

Isolation of 5' Region

To obtain the ZmAxig1 5' flanking region, endonuclease digested/adapter ligated (DL) libraries were prepared from maize genomic DNA (public inbred A632) using the Genome Walker™ kit (CLONTECH, Palo Alto, Calif.). DNA oligonucleotides, Primer 1 (SEQ ID No. 6) and Primer 2 (SEQ ID No. 7), were used along with the provided Genome Walker™ adapter primers for PCR amplification of the ZmAxig1 5' flanking region.

PCR products amplified from the ScaI and StuI DL libraries were cloned into the TOPO™ TA cloning vector (Invitrogen, Carlsbad, Calif.). The PCR reactions were repeated with the Genome Walker™ adapter primers and with DNA oligonucleotides Primer 3 (Seq. ID No. 8) or Primer 4 (Seq. ID No. 9), which span the putative start codon for the ZmAxig1 gene. Primer 4 is a synthetic oligo to create a NcoI restriction site at the start codon of ZmAxig1. The PCR products were cloned into the TOPO™ TA cloning vector as described above.

To confirm the sequence, the ZmAxig1 5' region was PCR amplified from maize genomic DNA using Pwo DNA polymerase (Boehringer Mannheim, Indianapolis, Ind.) with Primer 4 (Seq. ID No. 9) and another gene-specific primer, Primer 5 (Seq. ID No. 10). PCR products (~1.3 kb) were cloned into the pCR Blunt™ vector (Invitrogen, Carlsbad, Calif.) and sequenced.

EXAMPLE 4

Fertility Restoration using the ZmAxig1 Promoter

Two vectors were designed which differed in the size of the ZmAxig1 5' region included.

A first DNA plasmid was constructed by combining the ZmAxig1 promoter (SEQ ID NO: 24) with the Ms45 coding sequence and 35S:PAT in a T-DNA vector. This plasmid was cointegrated with Japan Tobacco plasmid pSB1 (Japan Tobacco, Inc; see U.S. Pat. No. 5,981,840) to create a first suitable vector, V1.

A second DNA plasmid was constructed by combining the ZmAxig1 promoter (1306 bases 5' of the start codon: SEQ ID NO:16) with the Ms45 coding sequence and 35S:PAT in a T-DNA vector. This plasmid was cointegrated with Japan Tobacco plasmid pSB1 to create a second suitable vector, V2.

Maize GS3Ms45EX4 embryos, segregating for homozygous ms45 (male sterile) and Ms45/ms45 (male fertile) genotypes, were transformed with the first and second vectors using Agrobacterium.

Figure 8:
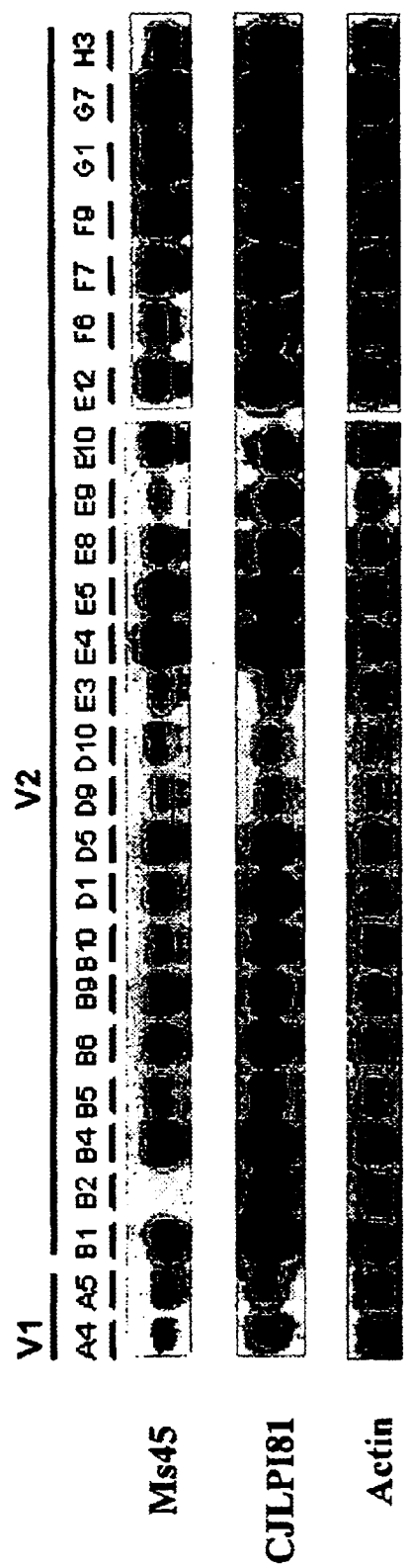
FIG. 8 shows Northern blot analyses of cell lines transformed with V1 or V2.

RNA was isolated, as described above, from two callus lines transformed with V1 and 24 callus lines transformed with V2. Northern analyses showed that the Ms45 transgene is expressed in both of the V1 transformed lines and 23 of the 24 V2 transformed lines (FIG. 8). This shows that the ZmAxig1 promoter is able to drive expression of transgenes in maize cells cultured on medium containing the synthetic auxin 2,4-D.

Transformed cell lines homozygous for the ms45 male sterile genotype were screened by quantitative PCR screening and advanced for regeneration into plants. Positive lines were transferred to 289B medium, an MS-based medium containing bialaphos and carbenicillin, with lower sucrose and hormone levels, to initiate plant regeneration. Following somatic embryo maturation (2–3 weeks), well-developed somatic embryos were transferred to medium for germination and transferred to the lighted culture room. Approximately 7 days later, developing plantlets were transferred to medium in tubes for 7 days until plantlets were well established. Plants were then transferred to inserts in flats (equivalent to 2.5" pot) containing potting soil and grown for one week in a growth chamber, subsequently grown an additional 1–2 weeks in the greenhouse, then transferred to classic 600 pots (1.6 gallon) and grown to maturity.

From each of 20 independent callus lines transformed with V2, six regenerated plants were grown in the greenhouse. When anthers approached quartet stage of microspore development, plants were treated with a daily soil drench (200 to 450 ml of water containing 3 μl dicamba formulation), for one, two or three days, or were not treated. The plants were scored for fertility after tassels emerged. Of 39 non-treated plants, 36 were sterile, 1 exerted a few anthers containing pollen (partially fertile, also known as "shedder" phenotype) and 2 did not have tassels that could be scored. Of 81 plants that were treated with dicamba, 69 plants produced anthers with pollen (36 shedder, 33 fertile). Pollen from 9 dicamba-treated plants was used to pollinate ears of non-transformed plants, resulting in kernels which germinated into plants, indicating that the pollen was viable.

To observe if other synthetic auxins are able to induce male fertility in pZmAxig1:Ms45 plants with male sterile genotype, homozygous ms45 (male sterile) V2 transgenic progeny were treated with 10 μl clopyralid formulation (Stinger®, 40.9% active ingredient clopyralid) in foliar applications with 1 ml water, soil drench applications with 200 ml water, or were not treated. Two of five plants treated with foliar applications of clopyralid, and three of six plants treated with clopyralid soil drench applications, showed partial to complete male fertile phenotypes. The nine non-treated plants remained male sterile.

EXAMPLE 5

Obtaining Full-Length Sequence of ZmAxig1

To obtain the full-length sequence of the ZmAxig1 gene, SEQ ID. No.12 was used to screen a B73 genomic library. This library was made by cloning Sau3AI partially digested genomic DNA into a BamHI digested genomic cloning vector (Lambda Dash II, Stratagene, La Jolla, Calif.). Approximately $1 \times 10^6$ plaques were screened using an E. coli strain suitable for genomic DNA (ER1647, New England Biolabs, MA) as the host. Clone 10.1 was purified to homogeneity after three rounds of screening. Southern blot analysis showed that an EcoRI/SacI fragment of about 4 kb in length hybridized with SEQ ID. No.12. This fragment was subcloned to a cloning vector (Bluescript SK+, Statagene, La Jolla, Calif.) and sequenced. This clone contained part of the Lambda DashII vector as well as sequence homologous to all except the first 408 nucleotides of SEQ ID. No. 1.

Primer 6 (SEQ ID No. 14) and primer 7 (SEQ ID No. 15) were used to PCR amplify a 2.2 kb fragment from maize genomic DNA using Pfx DNA polymerase (Life Technologies, Inc., Rockville, Md.). This fragment overlaps the ZmAxig1 5' region and includes the entire coding sequence and the 3' flanking region of the gene.

FIG. 9 is a GAP comparison of the full-length ZmAxig1 sequence (Sequence ID No. 5) and the CZAAL47 sequence (Sequence ID No. 1).

EXAMPLE 6

Use of pZmAxig1::LEC1 to Confer a Growth Advantage in Tissue Culture

Transformation was performed as follows: Using the genotype High type II (Hi-II) as an example, ears were surface sterilized in 30% Clorox bleach plus 0.5% Micro detergent for 20 minutes, and rinsed three times with sterile water. The immature embryos were excised and placed embryo axis side down (scutellum side up), 25 embryos per plate, and cultured for 3–5 days on 560P medium, an N6-based medium containing Eriksson's vitamins, thiamine, sucrose, 2,4-D (2 mg/L), and silver nitrate. Two to twelve hours before bombardment these embryos were transferred to high osmotic 560Y medium, N6-based medium containing Eriksson's vitamins, thiamine, 12% sucrose, 2,4-D (1 mg/L), and silver nitrate. Plasmid DNA was precipitated onto 1.0 m (average diameter) gold pellets using a $CaCl_2$ precipitation procedure as follows: 50 1 prepared gold particles in water, 10 1 DNA (used at a concentration of 0.1 g/l) in Tris EDTA buffer (1 g total), 5012.5 M $CaCl_2$, 20 10.1 M spermidine. Each reagent was added sequentially to the gold particle suspension, while maintained on the multi-tube vortexer. The final mixture was sonicated briefly and allowed to incubate under constant vortexing for 10 minutes. After the precipitation period, the tubes were centrifuged briefly, liquid removed, washed with 250 11001% ethanol, and centrifuged for 30 seconds. Again the liquid was removed, and 30 1100% ethanol was added to the final gold particle slurry. For particle gun bombardment, the gold/DNA particles were briefly sonicated and 5 1 spotted onto the center of eachmacrocarrier and allowed to dry about 2 minutes before bombardment.

The sample plates were bombarded at level #4 using a Dupont biolistics particle gun. All samples received a single shot at 650 PSI, with a total of six aliquots taken from each tube of prepared particles/DNA. Expression cassettes containing the ZmAxig1-driven LEC1 cDNA (see WO 00/28058) were co-introduced into the scutella of these embryos, along with an expression cassette containing the selectable marker gene PAT (Wohlleben et al. (1988) *Gene* 70:25–37) that confers resistance to the herbicide bialaphos, fused to the green fluorescence protein (GFP; see WO 95/07463), allowing selection on bialaphos-containing medium while observing transformation with GFP.

As a negative control, embryos were bombarded with the same PAT/GFP fusion construct along with either GUS or a frameshift version of LEC 1. For a positive control, embryos were shot with LEC1 driven by the Ubiquitin promoter.

Twelve to 24 hours following bombardment, embryos were then transferred back to 560P culture medium and incubated in the dark at 26° C. After one week of culture these embryos were moved to 560R selection medium, an N6-based medium containing Eriksson's vitamins, thiamine, sucrose, 2,4-D (2 mg/L), silver nitrate, and Bialaphos (3 mg/L). Cultures were then transferred every two weeks until transformed colonies appeared.

As shown in FIG. 11, ZmAxig1-driven LEC1 expression stimulated somatic embryogenesis in Hi-II cultures, as evidenced by increased transformation frequencies. This was apparent when the cultures were compared to controls (transformed without the LEC1 cDNA). In most cases, pZmAxig1::LEC1 stimulated transformation frequencies to a level comparable to or better than that observed with the ubiquitin promoter.

EXAMPLE 7

Use of ZmAxig1 to Restrict Expression of Transformants

The anther-preferred nature of the ZmAxig1 promoter allows design of transgenic systems to downregulate gene expression in developing microspores. For example, a construct combining the auxin-induced, anther-preferred ZmAxig1 promoter with a structural gene in antisense orientation would provide inducible, tissue-preferred restriction of expression of native genes or transgenes which are otherwise constitutively expressed.

EXAMPLE 8

Construction of a cDNA Library

Total RNA can be isolated from maize tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples are pulverized in liquid nitrogen before the addition of the TRIzol Reagent, and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+ RNA from total RNA can be performed using PolyATact system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water. cDNA synthesis and construction of unidirectional cDNA libraries can be accomplished using the SuperScript Plasmid System (Life Technology Inc. Gaithersburg, Md.). The first strand of cDNA is synthesized by priming an oligo(dT) primer containing a Not I site. The reaction is catalyzed by SuperScript Reverse Transcriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by Sephacryl-S400 chromatography. The selected cDNA molecules are ligated into pSPORT1 vector in between of Not I and Sal I sites.

Alternatively, cDNA libraries can be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 9

Construction of a Full-Length Enriched cDNA Library

An enriched full-length cDNA library can be constructed using one of two variations of the method of Caminci et al. *Genomics* 37: 327–336, 1996. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "Super-Script Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

A. First Strand cDNA Synthesis Method 1 (with trehalose)

| | |
|---|---|
| mRNA (10 ug) | 25 µl |
| *Not I primer (5 ug) | 10 µl |
| *5x 1$^{st}$ strand buffer | 43 µl |
| *0.1m DTT | 20 µl |

-continued

| *dNTP mix 10 mm | 10 µl |
|---|---|
| BSA 10 ug/µl | 1 µl |
| Trehalose (saturated) | 59.2 µl |
| RNase inhibitor (Promega) | 1.8 µl |
| *Superscript II RT 200 u/µl | 20 µl |
| 100% glycerol | 18 µl |
| Water | 7 µl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| Step 1 | 45° C. 10 min |
|---|---|
| Step 2 | 45° C. −0.3° C./cycle , 2 seconds/cycle |
| Step 3 | go to 2 for 33 cycles |
| Step 4 | 35° C. 5 min |
| Step 5 | 45° C. 5 min |
| Step 6 | 45° C. 0.2° C./cycle, 1 sec/cycle |
| Step 7 | go to 7 for 49 cycles |
| Step 8 | 55° C. 0.1° C./cycle, 12 sec/cycle |
| Step 9 | go to 8 for 49 cycles |
| Step 10 | 55° C. 2 min |
| Step 11 | 60° C. 2 min |
| Step 12 | go to 11 for 9 times |
| Step 13 | 4° C. forever |
| Step 14 | end |

B. First Strand cDNA Synthesis Method 2

| mRNA (10 µg) | 25 µl |
|---|---|
| water | 30 µl |
| *Not I adapter primer (5 µg) | 10 µl |
| 65° C. for 10 min, chill on ice, then add following reagents, | 20 µl |
| *5x first buffer | |
| *0.1M DTT | 10 µl |
| *10 mM dNTP mix | 5 µl |

Incubate at 45° C. for 2 min, then add 10 µl of *Superscript II RT (200 u/µl), start the following program:

| Step 1 | 45° C. for 6 sec, −0.1° C./cycle |
|---|---|
| Step 2 | go to 1 for 99 additional cycles |
| Step 3 | 35° C. for 5 min |
| Step 4 | 45° C. for 60 min |
| Step 5 | 50° C. for 10 min |
| Step 6 | 4° C. forever |
| Step 7 | end |

After the $1^{st}$ strand cDNA synthesis, the DNA is extracted by phenol according to standard procedures, and then precipitated in NaOAc and ethanol, and stored in −20° C.

C. Oxidization of the Diol Group of mRNA for Biotin Labeling

First strand cDNA is spun down and washed once with 70% EtOH. The pellet resuspended in 23.2 µl of DEPC treated water and put on ice. Prepare 100 mM of NaIO4 freshly, and then add the following reagents:

| mRNA:$1^{st}$ cDNA (start with 20 µg mRNA) | 46.4 µl |
|---|---|
| 100 mM NaIO4 (freshly made) | 2.5 µl |
| NaOAc 3M pH 4.5 | 1.1 µl |

To make 100 mM NaIO4, use 21.39 µg of NaIO4 for 1 µl of water. Wrap the tube in a foil and incubate on ice for 45 min. After the incubation, the reaction is then precipitated in:

| 5M NaCL | 10 µl |
|---|---|
| 20% SDS | 0.5 µl |
| isopropanol | 61 µl |

Incubate on ice for at least 30 min, then spin it down at max speed at 4° C. for 30 min and wash once with 70% ethanol and then 80% EtOH.
D. Biotinylation of the mRNA Diol Group
Resuspend the DNA in 110 µl DEPC treated water, then add the following reagents:

| 20% SDS | 5 µl |
|---|---|
| 2M NaOAc pH 6.1 | 5 µl |
| 10 mm biotin hydrazide (freshly made) | 300 µl |

Wrap in a foil and incubate at room temperature overnight.
E. RNase I Treatment
Precipitate DNA in:

| 5M NaCl | 10 µl |
|---|---|
| 2M NaOAc pH 6.1 | 75 µl |
| biotinylated mRNA:cDNA | 420 µl |
| 100% EtOH (2.5 Vol) | 1262.5 µl |

(Perform this precipitation in two tubes and split the 420 µl of DNA into 210 µl each, add 5 µl of 5M NaCl, 37.5 µl of 2M NaOAc pH 6.1, and 631.25 µl of 100% EtOH). Store at −20° C. for at least 30 min. Spin the DNA down at 4° C. at maximal speed for 30 min. and wash with 80% EtOH twice, then dissolve DNA in 70 µl RNase free water. Pool two tubes and end up with 140 µl.
Add the following reagents:

| RNase One 10 U/µl | 40 µl |
|---|---|
| $1^{st}$ cDNA:RNA | 140 µl |
| 10X buffer | 20 µl |

Incubate at 37° C. for 15 min.
Add 5 µl of 40 µg/µl yeast tRNA to each sample for capturing.
F. Full Length $1^{st}$ cDNA Capturing
Blocking the beads with yeast tRNA:

| Beads | 1 ml |
|---|---|
| Yeast tRNA 40 µg/µl | 5 µl |

Incubate on ice for 30 min with mixing, wash 3 times with 1 ml of 2M NaCl, 50 mmEDTA, pH 8.0.
Resuspend the beads in 800 µl of 2M NaCl, 50 mm EDTA, pH 8.0, add RNase I treated sample 200 µl, and incubate the reaction for 30 min at room temperature.

Capture the beads using the magnetic stand, save the supernatant, and start following washes:

2 washes with 2M NaCl, 50 mm EDTA, pH 8.0, 1 ml each time,
1 wash with 0.4% SDS, 50 μg/ml tRNA,
1 wash with 10 mm Tris-Cl pH 7.5, 0.2 mm EDTA, 10 mm NaCl, 20% glycerol,
1 wash with 50 μg/ml tRNA,
1 wash with $1^{st}$ cDNA buffer G. Second Strand cDNA Synthesis Resuspend the beads in:

| | |
|---|---|
| *5X first buffer | 8 μl |
| *0.1 mM DTT | 4 μl |
| *10 mm dNTP mix | 8 μl |
| *5X 2nd buffer | 60 μl |
| *E. coli Ligase 10 U/μl | 2 μl |
| *E. coli DNA polymerase 10 U/μl | 8 μl |
| *E. coli RNaseH 2U/μl | 2 μl |
| P32 dCTP 10 μci/μl | 2 μl |
| Or water up to 300 μl | 208 μl |

Incubate at 16° C. for 2 hr with mixing the reaction in every 30 min.

Add 4 μl of T4 DNA polymerase and incubate for additional 5 min at 16° C.

Elute $2^{nd}$ cDNA from the beads.

Use a magnetic stand to separate the $2^{nd}$ cDNA from the beads, then resuspend the beads in 200 μl of water, and then separate again, pool the samples (about 500 μl), Add 200 μl of water to the beads, then 200 μl of phenol:chloroform, vortex, and spin to separate the sample with phenol.

Pool the DNA together (about 700 μl) and use phenol to clean the DNA again, DNA is then precipitated in 2 μg of glycogen and 0.5 vol of 7.5M NH4OAc and 2 vol of 100% EtOH. Precipitate overnight. Spin down the pellet and wash with 70% EtOH, air-dry the pellet.

| | | | |
|---|---|---|---|
| DNA | 250 μl | DNA | 200 μl |
| 7.5M NH4OAc | 125 μl | 7.5M NH4OAc | 100 μl |
| 100% EtOH | 750 μl | 100% EtOH | 600 μl |
| glycogen 1 μg/μl | 2 μl | glycogen 1 μg/μl | 2 μl |

H. Sal I Adapter Ligation

Resuspend the pellet in 26 μl of water and use 1 μl for TAE gel.

Set up reaction as following:

| | |
|---|---|
| $2^{nd}$ strand cDNA | 25 μl |
| *5X T4 DNA ligase buffer | 10 μl |
| *Sal I adapters | 10 μl |
| *T4 DNA ligase | 5 μl |

Mix gently, incubate the reaction at 16° C. overnight.

Add 2 μl of ligase second day and incubate at room temperature for 2 hrs (optional).

Add 50 μl water to the reaction and use 100 μl of phenol to clean the DNA, 90 μl of the upper phase is transferred into a new tube and precipitate in:

| | |
|---|---|
| Glycogen 1 μg/μl | 2 μl |
| Upper phase DNA | 90 μl |
| 7.5M NH4OAc | 50 μl |
| 100% EtOH | 300 μl | preciptate at −20° C. overnight

Spin down the pellet at 4° C. and wash in 70% EtOH, dry the pellet.

I. Not I Digestion

| | |
|---|---|
| $2^{nd}$ cDNA | 41 μl |
| *Reaction 3 buffer | 5 μl |
| *Not I 15 u/μl | 4 μl |

Mix gently and incubate the reaction at 37° C. for 2 hr.

Add 50 μl of water and 100 μl of phenol, vortex, and take 90 μl of the upper phase to a new tube, then add 50 μl of NH4OAc and 300 μl of EtOH. Precipitate overnight at −20° C.

Cloning, ligation, and transformation are performed per the Superscript cDNA synthesis kit.

EXAMPLE 10 cDNA Sequencing and Library Subtraction

Individual colonies can be picked and DNA prepared either by PCR with M13 forward primers and M13 reverse primers, or by plasmid isolation. cDNA clones can be sequenced using M13 reverse primers.

cDNA libraries are plated out on 22×22 $cm^2$ agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C. Once sufficient colonies are picked, they are pinned onto 22×22 $cm^2$ nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40–50 minutes. The filters are placed on dry filter papers to dry overnight. DNA is then cross-linked to nylon membrane by UV light treatment.

Colony hybridization is conducted as described by Sambrook, J., Fritsch, E. F. and Maniatis, T., (in Molecular Cloning: A laboratory Manual, $2^{nd}$ Edition). The following probes can be used in colony hybridization:

1. First strand cDNA from the same tissue as the library was made from, to remove the most redundant clones.
2. 48–192 most redundant cDNA clones from the same library based on previous sequencing data.
3. 192 most redundant cDNA clones in the entire maize sequence database.
4. A Sal-A20 oligo nucleotide: TCG ACC CAC GCG TCC GAA AAA AAA AAA AAA AAA AAA (Seq. ID No. 11) removes clones containing a poly A tail but no cDNA.

5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

EXAMPLE 11

Identification of the Gene from a Computer Homology Search

Gene identities can be determined by conducting BLAST (Basic Local Alignment Search Tool; Altschul, S. F., et al., (1993) J. Mol. Biol. 215:403–410; searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. Nature Genetics 3:266–272 (1993)) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

EXAMPLE 12

Expression of Transgenes in Monocot Cells

A transgene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL 1-Blue (Epicurian Coli XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; U.S. Biochemical). The resulting plasmid construct would comprise a transgene encoding, in the 5' to 3' direction, the maize 27 kD zein promoter, a cDNA fragment encoding the instant polypeptides, and the 10 kD zein 3' region.

The transgene described above can then be introduced into maize cells by the following procedure. Immature maize embryos can be dissected from developing caryopses derived from crosses of the inbred maize lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. Thepat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μl of a suspension of gold particles (60 mg per ml). Calcium chloride (50 μl of a 2.5 M solution) and spermidine free base (20 μl of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μl of absolute ethanol, centrifuged again and the supernatant removed. The ethanol rinse is performed again and the particles resuspended in a final volume of 30 μl of ethanol. An aliquot (5 μl) of the DNA-coated gold particles can be placed in the center of a Kapton flying disc (Bio-Rad Labs). The particles are then accelerated into the maize tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

EXAMPLE 13

Expression of Transgenes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/ml hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 14

Expression of a Transgene in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG low melting agarose gel (FMC). Buffer and agarose contain 10 μg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 μl of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One microgram of protein from the soluble fraction of the culture can be separated by SDS-polyacrylamide gel electrophoresis. Gels can be observed for protein bands migrating at the expected molecular weight.

The above examples are provided to illustrate the invention but not to limit its scope. Other applications of the invention will be readily apparent to one of ordinary skill in the art and are encompassed by the appended claims.

What is claimed is:

1. An isolated promoter responsive to the presence of auxin, wherein said promoter is selected from the group consisting of: SEQ ID NO: 3, SEQ ID NO. 4, SEQ ID NO:16, nucleotides 647–1307 of SEQ ID NO: 3, nucleotides 647–1307 of SEQ ID NO: 4, and nucleotides 647–1306 of SEQ ID NO: 16.

2. A recombinant expression cassette, comprising a polynucleotide of interest operably linked, in sense or anti-sense orientation, to the isolated promoter of claim 1.

3. A host cell comprising the recombinant expression cassette of claim 2.

4. A plant cell comprising the recombinant expression cassette of claim 2.

5. A transgenic plant comprising the plant cell of claim 4.

6. A transgenic seed from the transgenic plant of claim 5.

7. A method of altering the expression of a polynucleotide of interest in a plant, said method comprising stably incorporating into the genome of said plant the expression cassette of claim 2 and exposing said plant to an auxin, wherein the promoter induces transcription of the polynucleotide of interest.

8. The method of claim 7, wherein said transcription of the polynucleotide of interest occurs in one or more tissues selected from the group con slating of anther, tapetum, and meristem.

* * * * *

SEQUENCE LISTING

<160> NUMBER OF SEQ ID NOS: 26

<210> SEQ ID NO 1
<211> LENGTH: 1271
<212> TYPE: DNA
<213> ORGANISM: Zea mays
<220> FEATURE:
<221> NAME/KEY: CDS
<222> LOCATION: (170)...(763)

<400> SEQUENCE: 1

```
gcaggaactt atttgccgtg cgctcccagg tctccgctcg cgtgccttcc agtctgtctc       60
acactagctg ctgtgggacg atcgaagtgg gtgtgtcagc tagctagctg cgccgtgacc      120
acgcacatga ccgcagtgcg cgcggggctg atcaaggaa agtgatcgg atg gag ctg      178
                                                       Met Glu Leu
                                                         1 gag ctc ggg ctc gcg ccg ccg aac ccg cat cag ccg ctg gct gcc gcc       226
Glu Leu Gly Leu Ala Pro Pro Asn Pro His Gln Pro Leu Ala Ala Ala
      5                  10                  15 gcc gag ttc gtc ggt ctc ctc agc agc tcg gct ggc tcg tgc ggg aac       274
Ala Glu Phe Val Gly Leu Leu Ser Ser Ser Ala Gly Ser Cys Gly Asn
 20                  25                  30                  35 aag agg gtt ctc ggc gac gcg ttc ggg gcc gcc aag gcg gcc acg ctt       322
Lys Arg Val Leu Gly Asp Ala Phe Gly Ala Ala Lys Ala Ala Thr Leu
                 40                  45                  50 ccg ctc ttc gtc tgc gag gat ggc gac gga ggc ggc ggc gac cgc gac       370
Pro Leu Phe Val Cys Glu Asp Gly Asp Gly Gly Gly Gly Asp Arg Asp
             55                  60                  65 cgc gac ggc gtc gtc gac cat gaa cag caa agc aac aat gta ccc agg       418
Arg Asp Gly Val Val Asp His Glu Gln Gln Ser Asn Asn Val Pro Arg
         70                  75                  80 aag aag agg ctg gtg ggg tgg ccg ccg gtg aag tgc gcg cgt agg cgt       466
Lys Lys Arg Leu Val Gly Trp Pro Pro Val Lys Cys Ala Arg Arg Arg
     85                  90                  95 agc tgc ggc ggc ggg tac gtg aag gtg aag ctg gaa ggg gtg ccc atc       514
```

```
Ser Cys Gly Gly Gly Tyr Val Lys Val Lys Leu Glu Gly Val Pro Ile
100                 105                 110                 115 ggg cgg aag gtg gac gtg tcc atc cac ggc tcg tac cag gag ctg ctc        562
Gly Arg Lys Val Asp Val Ser Ile His Gly Ser Tyr Gln Glu Leu Leu
            120                 125                 130 cgc acg ctc gag agc atg ttc cct tcg ggt aac caa caa gat cat gca        610
Arg Thr Leu Glu Ser Met Phe Pro Ser Gly Asn Gln Gln Asp His Ala
                135                 140                 145 gaa gac gag gtg gtg gtc tcg cac gag cgc cgc cgt cgc cat cct tat        658
Glu Asp Glu Val Val Val Ser His Glu Arg Arg Arg Arg His Pro Tyr
            150                 155                 160 gta gtc acc tac gag gac ggc gaa ggg gac tgg ttg ctc gtc gga gat        706
Val Val Thr Tyr Glu Asp Gly Glu Gly Asp Trp Leu Leu Val Gly Asp
        165                 170                 175 gat gtg ccg tgg gag gtc ttt gtc aag tca gtg aag cgg ctc aag ata        754
Asp Val Pro Trp Glu Val Phe Val Lys Ser Val Lys Arg Leu Lys Ile
180                 185                 190                 195 ctt gcg tag ccgacggtcg cgcctcaga cgtcgtgt ggtccgtctc                   803
Leu Ala * accaggatcg gagcagtgta gtactcctgg cgtcatctg cgtaataacg ttgtttctgt        863
cctgtgtgcc cgtagcagta cgtactgtcc tatagtaagc tagctttatg gggtgcttca      923
gctttcagag catgacgaaa gcactgatta gctgctgtca tcacatttgg ttcgtctttg      983
tgtcgtacgg tatcgctggc gtcagtgtcg cggcagccta ggtgatctaa gcatacttac     1043
tatctcaagt tacttttggt ttcctgagct tgcatgtaa ttcatatacc gtatacgtgt      1103
gtgactcagg ggcgaagctg ccttaaggca caggggtcac cggacccgat ggaatttatc    1163
aaatccagta taaatacta tttaacactg ttcatcaata tatttgattt caataaaaaa     1223
aaaaaaaaaa aaaaaaaaaa aaaaaaaaaa aaaaaaaaaa aaaaaaaa                 1271

<210> SEQ ID NO 2
<211> LENGTH: 197
<212> TYPE: PRT
<213> ORGANISM: Zea mays

<400> SEQUENCE: 2

Met Glu Leu Glu Leu Gly Leu Ala Pro Pro Asn Pro His Gln Pro Leu
1               5                   10                  15

Ala Ala Ala Ala Glu Phe Val Gly Leu Leu Ser Ser Ser Ala Gly Ser
                20                  25                  30

Cys Gly Asn Lys Arg Val Leu Gly Asp Ala Phe Gly Ala Ala Lys Ala
            35                  40                  45

Ala Thr Leu Pro Leu Phe Val Cys Glu Asp Gly Asp Gly Gly Gly
        50                  55                  60

Asp Arg Asp Arg Asp Gly Val Val Asp His Glu Gln Gln Ser Asn Asn
65                  70                  75                  80

Val Pro Arg Lys Lys Arg Leu Val Gly Trp Pro Pro Val Lys Cys Ala
                85                  90                  95

Arg Arg Arg Ser Cys Gly Gly Tyr Val Lys Val Lys Leu Glu Gly
            100                 105                 110

Val Pro Ile Gly Arg Lys Val Asp Val Ser Ile His Gly Ser Tyr Gln
        115                 120                 125

Glu Leu Leu Arg Thr Leu Glu Ser Met Phe Pro Ser Gly Asn Gln Gln
    130                 135                 140

Asp His Ala Glu Asp Glu Val Val Val Ser His Glu Arg Arg Arg Arg
```

```
                145                 150                 155                 160
        His Pro Tyr Val Val Thr Tyr Glu Asp Gly Glu Gly Asp Trp Leu Leu
                        165                 170                 175
        Val Gly Asp Asp Val Pro Trp Glu Val Phe Val Lys Ser Val Lys Arg
                    180                 185                 190
        Leu Lys Ile Leu Ala
                195

<210> SEQ ID NO 3
<211> LENGTH: 1310
<212> TYPE: DNA
<213> ORGANISM: Zea mays

<400> SEQUENCE: 3
cccatcgctg ctttgtctac atcatgttct tcatcatcct ccccaggcga cgcgtgctgc    60
tgttcttatt cagactaccg ttcgagtgac tgcatggcgt acatctttct gcatcgactt   120
tgtacggcta catcgaacat atacacgaga tgtctcgtgt gaatagagtc actaatgcct   180
taagcatcgg ttactccgta gggtacattc tgttcttctt atttgtgcat atttttattg   240
ttgtttactg attatacgag tagttataca tacatgcaca tacatatcat cacatatatc   300
acaatatttt tctaaattaa attaaaacta aaaatgacta aatttctaac accaacgaca   360
ttgtaatgtt ttctccaaca actttaccta ttctacattg ttctatttcg aatttcactc   420
tataaacaac atagtctaca atggaaaaca gtgctttgta cgactatata cgcgatgtgt   480
ggctacaaca taagacaata tagtcgtttg aagattgaac ctatatatcg gtacggttaa   540
tccgtctatg tacgtgggca tgacgaacac ccgtgataac gaaggattaa cgtgcacaat   600
cataaatcca agtaggagc ggtgcatgat gagaatcgct ctcagtactc gacataatga    660
accttacgag gtacaacagg caggcaggca gggaccaggg gccgccttta tttcaggctc   720
gctggcccca cgggcgtgct gcgtgcacga agggcactac cccaacctct caccgaaaaa   780
ccgcgctgga tcggcaaatc aaacgaggtg gtgccccgtg cccactctcc acgtccacgg   840
caccatccct ctgcagccgc tcaccagcca tgccgtgtcg cggaacggca caaccacccc   900
caacccactc acgaaacccc gtcccggccg tgcccgtgtc ggtccgcgct cggcaacgag   960
gcggcccgcg ctgctgagtc ccctggacac ccgacaccct gtcggccctt tgtttattca  1020
tcccgaaatc tcatctgccc ccacggccga ctgcgctgcg ccgcccggat atatataccc  1080
atcgttatcg atcgatcgat cgcgtcactc acgggtagct catggtcgag cgtagcatgc  1140
aggaacttat ttgccgtgcg ctcccaggtc tccgctcgcg tgccttccag tctgtctcac  1200
actagctgct gtgggacgat cgaagtgggt gtgtcagcta gctagctgcg ccgtgaccac  1260
gcacatgacc gcagtgcgcg cggggctgat caagggaaag tgatcggatg              1310

<210> SEQ ID NO 4
<211> LENGTH: 1310
<212> TYPE: DNA
<213> ORGANISM: Zea mays

<400> SEQUENCE: 4
cccatcgctg ctttgtctac atcatgttct tcatcatcct ccccaggcga cgcgtgctgc    60
tgttcttatt cagactaccg ttcgagtgac tgcatggcgt acatctttct gcatcgactt   120
tgtacggcta catcgaacat atacacgaga tgtctcgtgt gaatagagtc actaatgcct   180
taagcatcgg ttactccgta gggtacattc tgttcttctt atttgtgcat atttttattg   240
```

```
ttgtttactg attatacgag tagttataca tacatgcaca tacatatcat cacatatatc      300
acaatatttt tctaaattaa attaaaacta aaaatgacta aatttctaac accaacgaca      360
ttgtaatgtt ttctccaaca actttaccta ttctacattg ttctatttcg aatttcactc      420
tataaacaac atagtctaca atggaaaaca gtgctttgta cgactatata cgcgatgtgt      480
ggctacaaca taagacaata tagtcgtttg aagattgaac ctatatatcg gtacggttaa      540
tccgtctatg tacgtgggca tgacgaacac ccgtgataac gaaggattaa cgtgcacaat      600
cataaatcca aagtaggagc ggtgcatgat gagaatcgct ctcagtactc gacataatga      660
accttacgag gtacaacagg caggcaggca gggaccaggg gccgccttta tttcaggctc      720
gctggcccca cgggcgtgct gcgtgcacga agggcactac cccaacctct caccgaaaaa      780
ccgcgctgga tcggcaaatc aaacgaggtg gtgccccgtg cccactctcc acgtccacgg      840
caccatccct ctgcagccgc tcaccagcca tgccgtgtcg cggaacggca caaccacccc      900
caacccactc acgaaacccc gtcccggccg tgcccgtgtc ggtccgcgct cggcaacgag      960
gcggcccgcg ctgctgagtc ccctggacac ccgacaccct gtcggccctt tgtttattca     1020
tcccgaaatc tcatctgccc ccacggccga ctgcgctgcg ccgcccggat atatataccc     1080
atcgttatcg atcgatcgat cgcgtcactc acgggtagct catggtcgag cgtagcatgc     1140
aggaacttat ttgccgtgcg ctcccaggtc tccgctcgcg tgccttccag tctgtctcac     1200
actagctgct gtgggacgat cgaagtgggt gtgtcagcta gctagctgcg ccgtgaccac     1260
gcacatgacc gcagtgcgcg cggggctgat caagggaaag tgatcccatg               1310
```

<210> SEQ ID NO 5
<211> LENGTH: 3123
<212> TYPE: DNA
<213> ORGANISM: Zea mays

<400> SEQUENCE: 5

```
cccatcgctg ctttgtctac atcatgttct tcatcatcct ccccaggcga cgcgtgctgc       60
tgttcttatt cagactaccg ttcgagtgac tgcatggcgt acatctttct gcatcgactt      120
tgtacggcta catcgaacat atacacgaga tgtctcgtgt gaatagagtc actaatgcct      180
taagcatcgg ttactccgta gggtacattc tgttcttctt atttgtgcat atttttattg      240
ttgtttactg attatacgag tagttataca tacatgcaca tacatatcat cacatatatc      300
acaatatttt tctaaattaa attaaaacta aaaatgacta aatttctaac accaacgaca      360
ttgtaatgtt ttctccaaca actttaccta ttctacattg ttctatttcg aatttcactc      420
tataaacaac atagtctaca atggaaaaca gtgctttgta cgactatata cgcgatgtgt      480
ggctacaaca taagacaata tagtcgtttg aagattgaac ctatatatcg gtacggttaa      540
tccgtctatg tacgtgggca tgacgaacac ccgtgataac gaaggattaa cgtgcacaat      600
cataaatcca aagtaggagc ggtgcatgat gagaatcgct ctcagtactc gacataatga      660
accttacgag gtacaacagg caggcaggca gggaccaggg gccgccttta tttcaggctc      720
gctggcccca cgggcgtgct gcgtgcacga agggcactac cccaacctct caccgaaaaa      780
ccgcgctgga tcggcaaatc aaacgaggtg gtgccccgtg cccactctcc acgtccacgg      840
caccatccct ctgcagccgc tcaccagcca tgccgtgtcg cggaacggca caaccacccc      900
caacccactc acgaaacccc gtcccggccg tgcccgtgtc ggtccgcgct cggcaacgag      960
gcggcccgcg ctgctgagtc ccctggacac ccgacaccct gtcggccctt tgtttattca     1020
tcccgaaatc tcatctgccc ccacggccga ctgcgctgcg ccgcccggat atatataccc     1080
```

-continued

```
atcgttatcg atcgatcgat cgcgtcactc acgggtagct catggtcgag cgtagcatgc   1140
aggaacttat tgccgtgcgc ctcccaggtc tccgctcgcg tgccttccag tctgtctcac   1200
actagctgct gtgggacgat cgaagtgggt gtgtcagcta gctagctgcg ccgtgaccac   1260
gcacatgacc gcagtgcgcg cggggctgat caagggaaag tgatcggatg gagctggagc   1320
tcgggctcgc gccgccgaac ccgcatcagc cgctggctgc cgccgccgag ttcgtcggtc   1380
tcctcagcag ctcggctggc tcgtgcggga acaagagggt tctcggcgac gcgttcgggg   1440
ccgccaaggc ggccacgctt ccgctcttcg tctgcgagga tggcgacgga ggcggcggcg   1500
accgcgaccg cgacggcgtc gtcgaccatg aacagcaaag caacaagtga gttgtggtta   1560
aaaataccga ccacgtgcgt acagggaggg tcttattata cccaaatccg atccgtggtg   1620
tgtgtagtgt acccaggaag aagaggctgg tggggtggcc gccggtgaag tgcgcgcgta   1680
ggcgtagctg cggcggcggg tacgtgaagg tgaagctgga aggggtgccc atcgggcgga   1740
aggtggacgt gtccatccac ggctcgtacc aggagctgct ccgcacgctc gagagcatgt   1800
tcccttcggg taaccaacaa ggtgcgtacg ttcccgggcc gcggcgagcc ggccggcgac   1860
cggcggtgct gcggacgatg cctttctttc actgataatc atctgccgcc atcgttctgg   1920
tcccgacacg tgcccttgct tcccgttctg ctcccggcac ttaacttggt cgcatatact   1980
attcctgtaa cctctggcag atcatgcaga agacgaggtg gtggtctcgc acgagcgccg   2040
ccgtcgccat ccttatgtag tcacctacga ggacggcgaa ggggactggt tgctcgtcgg   2100
agatgatgtg ccgtgggagt acgtatcagt cactactact gtcgtctgta tgactgtatc   2160
gatggtgacg gcaacaatat aatccaatta attattcagc gaacttaaaa acgacgttga   2220
tttccttgca gggtctttgt caagtcagtg aagcggctca agatacttgc gtagccgacg   2280
gtcggcgcct cagagacgtc gtgtggtccg tctcaccagg atcggagcag tgtagtactc   2340
ctgggcgtca tctgcgtaat aacgttgttt ctgtcctgtg tgcccgtagc agtacgtact   2400
gtcctatagt aagctagctt tatggggtgc ttcagctttc agagcatgac gaaagcactg   2460
attagctgct gtcatcacat ttggttcgtc tttgtgtcgt acggtatcgc tggcgtcagt   2520
gtcgcggcag cctaggtgat ctaagcatac ttactatctc aagttacttt tggtttcctg   2580
agcttgcatg gtaattcata taccgtatac gtgtgtgact caggggcgaa gctgccttaa   2640
ggcacagggg tcaccggacc cgatggaatt tatcaaatcc agtgtaaaat actatttaac   2700
actgttcatc aatatatttg atttcaataa ttcatggagc tgaccttgtg gatccatttt   2760
ctgtcttcgc ctctggtgtg actagtattt tggtttgact tttcactctg tataagatat   2820
atattatacc agcgagttta tcgactgcta gttttacaag aggcttaact ctttcaattg   2880
cttattttta ttgcaacaac acactcctcc gttgttgtgg tattagatgt ggttctgaat   2940
gtaaatgtca ttataggata taaatgtagt gtttcctagt tttaccctag cttttcgcatg  3000 catagtggga aagtgtacta actctcctca tgcagaaaga ggtgtggtat acctaacaaa   3060
atcatacatc actactaatc tacggataat atatataaac cgtagcgaca cacgagtgct   3120
tag                                                                 3123
```

<210> SEQ ID NO 6
<211> LENGTH: 28
<212> TYPE: DNA
<213> ORGANISM: Zea mays

<400> SEQUENCE: 6
agcagctagt gtgagacaga ctggaagg          28

<210> SEQ ID NO 7
<211> LENGTH: 28
<212> TYPE: DNA
<213> ORGANISM: Zea mays
<220> FEATURE:

<400> SEQUENCE: 7
gtacattgtt gctttgctgt tcatggtc          28

<210> SEQ ID NO 8
<211> LENGTH: 29
<212> TYPE: DNA
<213> ORGANISM: Zea mays

<400> SEQUENCE: 8
ctccagctcc atccgatcac tttcccttg          29

<210> SEQ ID NO 9
<211> LENGTH: 29
<212> TYPE: DNA
<213> ORGANISM: Zea mays

<400> SEQUENCE: 9
ctccagctcc atgggatcac tttcccttg          29

<210> SEQ ID NO 10
<211> LENGTH: 23
<212> TYPE: DNA
<213> ORGANISM: Zea mays

<400> SEQUENCE: 10
cgacccatcg ctgctttgtc tac          23

<210> SEQ ID NO 11
<211> LENGTH: 36
<212> TYPE: DNA
<213> ORGANISM: Zea mays
<220> FEATURE:
<223> OTHER INFORMATION: Designed oligonucleotide based upon the
      adapter sequence and poly T to remove clones which have a
      poly A tail but no cDNA.

<400> SEQUENCE: 11
tcgacccacg cgtccgaaaa aaaaaaaaaa aaaaaa          36

<210> SEQ ID NO 12
<211> LENGTH: 100
<212> TYPE: DNA
<213> ORGANISM: Zea mays

<400> SEQUENCE: 12
cgatcgaagt gggtgtgtca gctagctagc tgcgccgtga ccacgcacat gaccgcagtg          60 cgcgcgggc tgatcaaggg aaagtgatcg gatggagctg                              100

<210> SEQ ID NO 13
<211> LENGTH: 52
<212> TYPE: DNA
<213> ORGANISM: Zea mays

<400> SEQUENCE: 13
gctagctgcg ccgtgaccac gcacatgacc gcagtgcgcg cggggctgat ca               52

<210> SEQ ID NO 14
<211> LENGTH: 22
<212> TYPE: DNA
<213> ORGANISM: Zea mays

<400> SEQUENCE: 14
acaaccaccc ccaacccact ca                                            22

<210> SEQ ID NO 15
<211> LENGTH: 22
<212> TYPE: DNA
<213> ORGANISM: Zea mays

<400> SEQUENCE: 15
ctaagcactc gtgtgtcgct ac                                            22

<210> SEQ ID NO 16
<211> LENGTH: 1309
<212> TYPE: DNA
<213> ORGANISM: Zea mays

<400> SEQUENCE: 16
cccatcgctg ctttgtctac atcatgttct tcatcatcct ccccaggcga cgcgtgctgc     60
tgttcttatt cagactaccg ttcgagtgac tgcatggcgt acatctttct gcatcgactt    120
tgtacggcta catcgaacat atacacgaga tgtctcgtgt gaatagagtc actaatgcct    180
taagcatcgg ttactccgta gggtacattc tgttcttctt atttgtgcat atttttattg    240
ttgtttactg attatacgag tagttataca tacatgcaca tacatatcat cacatatatc    300
acaatatttt tctaaattaa attaaaacta aaaatgacta aatttctaac accaacgaca    360
ttgtaatgtt ttctccaaca actttaccta ttctacattg ttctatttcg aatttcactc    420
tataaacaac atagtctaca atggaaaaca gtgctttgta cgactatata cgcgatgtgt    480
ggctacaaca taagacaata tagtcgtttg aagattgaac ctatatatcg gtacggttaa    540
tccgtctatg tacgtgggca tgacgaacac ccgtgataac gaaggattaa cgtgcacaat    600
cataaatcca agtaggagc ggtgcatgat gagaatcgct ctcagtactc gacataatga     660
accttacgag gtacaacagg caggcaggca gggaccaggg gccgcctta tttcaggctc     720
gctggcccca cgggcgtgct gcgtgcacga agggcactac cccaacctct caccgaaaac    780
cgcgctggat cggcaaatca aacgaggtgg tgccccgtgc ccactctcca cgtccacggc    840
accatccctc tgcagccgct caccagccat gccgtgtcgc ggaacggcac aaccacccc     900
aacccactca cgaaacccg tcccggccgt gccgtgtcg gtccgcgctc ggcaacgagg     960
cggcccgcgc tgctgagtcc cctggacacc cgacaccctg tcggcccttt gtttattcat   1020
cccgaaatct catctgcccc cacggccgac tgcgctgcgc cgcccggata tatatccca    1080
tcgttatcga tcgatcgatc gcgtcactca cgggtagctc atggtcgagc gtagcatgca   1140
ggaacttatt tgccgtgcgc tcccaggtct ccgctcgcgt gccttccagt ctgtctcaca   1200
ctagctgctg tgggacgatc gaagtgggtg tgtcagctag ctagctgcgc cgtgaccacg   1260
cacatgaccg cagtgcgcgc ggggctgatc aagggaaagt gatcccatg                1309

<210> SEQ ID NO 17
<211> LENGTH: 1433
<212> TYPE: DNA
<213> ORGANISM: Zea mays

<400> SEQUENCE: 17

-continued

```
agctagagta gtagcctgtg cttgctaccc ctggtcaaca catcgtagcc tcctatattt      60
tcctaatctt caaataacca tctcaaaagt tttttaaaac atcttttgag gatatgtatc     120
ccatagccct agagcgctaa attgactact tttagtcgat taaaaggtat tagacatcct    180
tacaagtcct aagtatcaaa tcaccttcta tcggctatac acaactaacg gaagttatct    240
ctagtcacac taacttatgt cggtttccgc atggcagatc aaaattagct aacttttgtt    300
ggctaataag agcaattcca aaagaacgtg taaactaatc tcaaaacaga tattagttaa    360
gaatagtaat ttttcttact ccaacagttc cctcagtctt ccccaaaaaa ttaagcgttc    420
cgcatccaca gcctcctctc ggtcgtattt tggtgtgttt catccctccc caatccattt    480
ctcaacgtat cagatcatcc accgcctacg acgactgtac agtttgcgtc acatatcaca    540
tttaaaggaa ctgttggagt acccatcata attcactctt aaaaaatttt agcctgctct    600
caataatcaa ttgggggggt aaatttttta acatcctttc ggatctaatc caacttatgg    660
aagttagcta gctctggtcg cgctaacttc tgtcgatcgc ctattagcta atactccatc    720
tgtcccatta tataaggtat aaccaactct gattcaaaga ccaaaaatat acttaattgt    780
gtctatacca cttcatcgat gtacgtatgc atagaaagag cacatcttat attgtggaac    840
aagaacaaaa atatggttac gccttatatt ataagacgta gaaatcaatg gtttacaata    900
gccaagaata gatgttttta tttatttcct atatagatgt ttttatttat ttcctatatg    960
tttcacaata gccttatatt gtgccgaaaa tttaggcaca cgtgccacga acgtctgaaa   1020
tgtactccgc gcgtattacc atgcactacg acgtacgtag gagtatgtac gttgaaccaa   1080
gcacacatat atctctgaca cagtacaatg atatactaca acaacaacag tactgcccaa   1140
ttcatccatt ttcacgttcc atcttccgcg tgtgacaact cgatcggcca cgcacgcaga   1200
cgacgacgga gcagtacttc acagaatcct ccgccactcg tcacaccaac aggcgcgcgc   1260
tggtgcgcat gcatcatgtg catgccatcg tccgtccctt ggcgtgcctc ggtagacggt   1320
aacgtatcct cacacatcac aagaacgaca cacagaaacc agtagccact actccatcca   1380
ccacgagcga gcgagcgata accctagcta gcttcaggat ccagcgagag ccc          1433
```

<210> SEQ ID NO 18
<211> LENGTH: 1173
<212> TYPE: DNA
<213> ORGANISM: Zea mays

<400> SEQUENCE: 18

```
ccacgcgtcc gccaccacac cacgagcgcg cgataaccct agctagcttc aggtagtagc     60
gagagccaat ggactccagc agcttcctcc ctgccgccgg cgcggagaat ggctcggcgg    120
cgggcggcgc caacaatggc ggcgctgctc agcagcatgc ggcgccggcg atccgcgagc    180
aggaccggct gatgccgatc gcgaacgtga tccgcatcat cgggcgcgtg ctgccggcgc    240
acgccaagat ctcggacgac gccaaggaga cgatccagga gtgcgtgtcg gagtacatca    300
gcttcatcac gggggaggcc aacgagcggt gccagcggga gcagcgcaag accatcaccg    360
ccgaggacgt gctgtgggcc atgagccgcc tcggcttcga cgactacgtc gagccgctcg    420
gcgcctacct ccaccgctac cgcgagttcg agggcgacgc gcgcggcgtc gggctcgtcc    480
cgggggccgc cccatcgcgc ggcggcgacc accaccgca ctccatgtcg ccagcggcga    540
tgctcaagtc ccgcgggcca gtctccggag ccgccatgct accgcaccac caccaccacc    600
acgacatgca gatgcacgcc gccatgtacg ggggaacggc cgtgccccg ccggccgggc   660
```

-continued

```
ctcctcacca cggcgggttc ctcatgccac acccacaggg tagtagccac tacctgcctt      720
acgcgtacga gcccacgtac ggcggtgagc acgccatggc tgcatactat ggaggcgccg      780
cgtacgcgcc cggcaacggc gggagcggcg acggcagtgg cagtggcggc ggtggcggga      840
gcgcgtcgca cacaccgcag ggcagcggcg gcttggagca cccgcacccg ttcgcgtaca      900
agtagctagt tcgtacgtcg ttcgacttga gcaagccatc gatctgctga tctgaacgta      960
cgctgtattg tacacgcatg cacgtacgta tcggcggcta gctctcctgt ttaagttgta     1020
ctgtgattct gtcccggccg gctagcaact tagtatcttc cttcagtctc tagtttctta     1080
gcagtcgtag aagtgttcaa tgcttgccag tgtgttgttt tagggccggg gtaaaccatc     1140
cgatgagatt atttcaaaaa aaaaaaaaaa aaa                                 1173
```

<210> SEQ ID NO 19
<211> LENGTH: 763
<212> TYPE: DNA
<213> ORGANISM: Zea mays

<400> SEQUENCE: 19

```
gcacgaggca agaccgtcac ctccgaggac atcgtgtggg ccatgagccg cctcggcttc       60
gacgactacg tcgcgcccct cggcgccttc ctccagcgca tgcgcgacga cagcgaccac      120
ggcggtgaag agcgcggcgg ccctgcaggg cgtggtggct cgcgccgcgg ctcgtcgtcc      180
ttgccgctcc actgcccgca gcagatgcac cacctgcacc cagccgtctg ccggcgtccg      240
caccagagcg tgtcgcctgc tgcaggatac gccgtccggc ccgttccccg cccgatgcca      300
gcccgtgggt accgcatgca gggcggagac caccgcagcg tgggcggcgt ggctccctgc      360
agctacggag gggcgctcgt ccaggccggt ggaacccaac acgttgttgg attccacgac      420
gacgaggcaa gctcttcgag tgaaaatccg ccgccggagg ggcgtgccgc tggctcgaac      480
tagcctagct tctcagttcc ccgtgtacaa taagaggggc ggtcgcggcg ccgcgccgcg      540
cccttgggtt gggccgggcg ctatgctgca gtttggtttg taaactaacg agcctagggt      600
agctggtgca cgcgcgccac ctcgccggac gtcgccgtcg tcgtcggcat ggacttaacc      660
ggcgggccct gttgttattt ctcaagtttg tagccaacgc actgttcggt gcgttccata      720
atttaattta ccatgttgct ctcgaaaaaa aaaaaaaaaa aaa                       763
```

<210> SEQ ID NO 20
<211> LENGTH: 622
<212> TYPE: DNA
<213> ORGANISM: Zea mays
<220> FEATURE:
<221> NAME/KEY: misc_feature
<222> LOCATION: (1)...(622)
<223> OTHER INFORMATION: n = a, t, c, or g

<400> SEQUENCE: 20

```
gcatgaataa tccccaaaac cctaaagcca gtgctccttg caccttgcca ccggagcttc       60
ccaaagaagc agtggcgacc gacgaagcac cgccgccaat gggcaacaac aacaacacgg      120
aatcggcgac ggcgacgatg gtccgggagc aggaccggct gatgcccgtg ccaacgtgt       180 cccgcatcat gcgccaagtg ctgcctccgt acgccaagat ctccgacgac gcccangaag      240
tnatccaaga attgctnttc ggaatttcat cacttncgtc ctggcgaggc gaaacgaagc      300
ggtgccacac cgagcgccgc aagaccgtca cctccgaaga catcgtgtgg gccatgagcc      360
gcctcggctt cgacgactac gtcgcgcccc tcggcgcctt cctccagcgc atgcgcgacn      420
acagcgaaca cgggggtgaa aacgcggcgg cctgcanggg gtngtggtcn cgccgcgggt      480
```

-continued

```
cgtctncttg gcgctcccTT gccgcaanag atgacaactt gcaccaaacg tctgccgggn    540
tcggaccaaa actnttccct gttgcaggaa tacccgtccn gggccnttcc ccccnaatc    600 caaccatttg gtttcccctt gc                                              622
```

```
<210> SEQ ID NO 21
<211> LENGTH: 65
<212> TYPE: PRT
<213> ORGANISM: Zea mays
<220> FEATURE:
<221> NAME/KEY: VARIANT
<222> LOCATION: (1)...(65)
<223> OTHER INFORMATION: Xaa = any amino acid

<400> SEQUENCE: 21
```

Arg Glu Gln Asp Xaa Xaa Met Pro Ile Ala Asn Val Ile Arg Ile Met
 1               5                  10                  15

Arg Xaa Xaa Leu Pro Xaa His Ala Lys Ile Ser Asp Asp Ala Lys Glu
             20                  25                  30

Xaa Ile Gln Glu Cys Val Ser Glu Tyr Ile Ser Phe Xaa Thr Xaa Glu
         35                  40                  45

Ala Asn Xaa Arg Cys Xaa Xaa Xaa Xaa Arg Lys Thr Xaa Xaa Xaa Glu
     50                  55                  60

Xaa
 65

```
<210> SEQ ID NO 22
<211> LENGTH: 1309
<212> TYPE: DNA
<213> ORGANISM: Zea mays

<400> SEQUENCE: 22
cccatcgctg ctttgtctac atcatgttct tcatcatcct ccccaggcga cgcgtgctgc     60
tgttcttatt cagactaccg ttcgagtgac tgcatggcgt acatctttct gcatcgactt    120
tgtacggcta catcgaacat atacacgaga gtgtctcgtgt gaatagagtc actaatgcct   180
taagcatcgg ttactccgta gggtacattc tgttcttctt atttgtgcat attttttattg   240 ttgtttactg attatacgag tagttataca tacatgcaca tacatatcat cacatatatc    300
acaatatttt tctaaattaa attaaaacta aaatgactaa aatttctaac accaacgaca    360
ttgtaatgtt ttctccaaca actttaccta ttctacattg ttctatttcg aatttcactc    420
tataaacaac atagtctaca atggaaaaca gtgctttgta cgactatata cgcgatgtgt    480
ggctacaaca taagacaata tagtcgtttg aagattgaac ctatatatcg gtacggttaa    540
tccgtctatg tacgtgggca tgacgaacac ccgtgataac gaaggattaa cgtgcacaat    600
cataaatcca agtaggagc ggtgcatgat gagaatcgct ctcagtactc gacataatga    660
accttacgag gtacaacagg caggcaggca gggaccaggg gccgccttta tttcaggctc    720
gctggcccca cgggcgtgct gcgtgcacga agggcactac cccaacctct caccgaaaac    780
cgcgctggat cggcaaatca aacgaggtgg tgccccgtgc ccactctcca cgtccacggc    840
accatccctc tgcagccgct caccagccat gccgtgtcgc ggaacggcac aaccacccccc  900 aacccactca cgaaacccccg tcccggccgt gcccgtgtcg gtccgcgctc ggcaacgagg    960
cggcccgcgc tgctgagtcc cctggacacc cgacaccctg tcggcccttt gtttattcat   1020
cccgaaatct catctgcccc cacggccgac tgcgctgcgc cgcccggata tatatacccca   1080 tcgttatcga tcgatcgatc gcgtcactca cgggtagctc atggtcgagc gtagcatgca   1140
```

```
ggaacttatt tgccgtgcgc tcccaggtct ccgctcgcgt gccttccagt ctgtctcaca    1200
ctagctgctg tgggacgatc gaagtgggtg tgtcagctag ctagctgcgc cgtgaccacg    1260
cacatgaccg cagtgcgcgc ggggctgatc aagggaaagt gatcggatg                1309
```

<210> SEQ ID NO 23
<211> LENGTH: 664
<212> TYPE: DNA
<213> ORGANISM: Zea mays

<400> SEQUENCE: 23

```
actcgacata atgaaccttta cgaggtacaa caggcaggca ggcagggacc aggggccgcc    60
tttatttcag gctcgctggc cccacgggcg tgctgcgtgc acgaagggca ctaccccaac    120
ctctcaccga aaaccgcgc tggatcggca aatcaaacga ggtggtgccc cgtgcccact     180
ctccacgtcc acggcaccat ccctctgcag ccgctcacca gccatgccgt gtcgcggaac    240
ggcacaacca cccccaaccc actcacgaaa ccccgtcccg gccgtgcccg tgtcggtccg    300
cgctcggcaa cgaggcggcc cgcgctgctg agtcccctgg acacccgaca ccctgtcggc    360
cctttgttta ttcatcccga aatctcatct gcccccacgg ccgactgcgc tgcgccgccc    420
ggatatatat acccatcgtt atcgatcgat cgatcgcgtc actcacgggt agctcatggt    480
cgagcgtagc atgcaggaac ttatttgccg tgcgctccca ggtctccgct cgcgtgcctt    540
ccagtctgtc tcacactagc tgctgtggga cgatcgaagt gggtgtgtca gctagctagc    600
tgcgccgtga ccacgcacat gaccgcagtg cgcgcggggc tgatcaaggg aaagtgatcg    660
gatg                                                                 664
```

<210> SEQ ID NO 24
<211> LENGTH: 664
<212> TYPE: DNA
<213> ORGANISM: Zea mays

<400> SEQUENCE: 24

```
actcgacata atgaaccttta cgaggtacaa caggcaggca ggcagggacc aggggccgcc    60
tttatttcag gctcgctggc cccacgggcg tgctgcgtgc acgaagggca ctaccccaac    120
ctctcaccga aaaccgcgc tggatcggca aatcaaacga ggtggtgccc cgtgcccact     180
ctccacgtcc acggcaccat ccctctgcag ccgctcacca gccatgccgt gtcgcggaac    240
ggcacaacca cccccaaccc actcacgaaa ccccgtcccg gccgtgcccg tgtcggtccg    300
cgctcggcaa cgaggcggcc cgcgctgctg agtcccctgg acacccgaca ccctgtcggc    360
cctttgttta ttcatcccga aatctcatct gcccccacgg ccgactgcgc tgcgccgccc    420
ggatatatat acccatcgtt atcgatcgat cgatcgcgtc actcacgggt agctcatggt    480
cgagcgtagc atgcaggaac ttatttgccg tgcgctccca ggtctccgct cgcgtgcctt    540
ccagtctgtc tcacactagc tgctgtggga cgatcgaagt gggtgtgtca gctagctagc    600
tgcgccgtga ccacgcacat gaccgcagtg cgcgcggggc tgatcaaggg aaagtgatcc    660
catg                                                                 664
```

<210> SEQ ID NO 25
<211> LENGTH: 663
<212> TYPE: DNA
<213> ORGANISM: Zea mays

<400> SEQUENCE: 25

```
                                                -continued actcgacata atgaacctta cgaggtacaa caggcaggca ggcagggacc aggggccgcc      60
tttatttcag gctcgctggc cccacgggcg tgctgcgtgc acgaagggca ctaccccaac     120
ctctcaccga aaaccgcgct ggatcggcaa atcaaacgag gtggtgcccc gtgcccactc     180
tccacgtcca cggcaccatc cctctgcagc cgctcaccag ccatgccgtg tcgcggaacg     240
gcacaaccac ccccaaccca ctcacgaaac cccgtcccgg ccgtgcccgt gtcggtccgc     300
gctcggcaac gaggcggccc gcgctgctga gtcccctgga cacccgacac cctgtcggcc     360
ctttgtttat tcatcccgaa atctcatctg cccccacggc cgactgcgct gcgccgcccg     420
gatatatata cccatcgtta tcgatcgatc gatcgcgtca ctcacgggta gctcatggtc     480
gagcgtagca tgcaggaact tatttgccgt gcgctcccag gtctccgctc gcgtgccttc     540
cagtctgtct cacactagct gctgtgggac gatcgaagtg ggtgtgtcag ctagctagct     600
gcgccgtgac cacgcacatg accgcagtgc gcgcggggct gatcaaggga aagtgatcgg     660
atg                                                                  663

<210> SEQ ID NO 26
<211> LENGTH: 663
<212> TYPE: DNA
<213> ORGANISM: Zea mays

<400> SEQUENCE: 26
actcgacata atgaacctta cgaggtacaa caggcaggca ggcagggacc aggggccgcc      60
tttatttcag gctcgctggc cccacgggcg tgctgcgtgc acgaagggca ctaccccaac     120
ctctcaccga aaaccgcgct ggatcggcaa atcaaacgag gtggtgcccc gtgcccactc     180
tccacgtcca cggcaccatc cctctgcagc cgctcaccag ccatgccgtg tcgcggaacg     240
gcacaaccac ccccaaccca ctcacgaaac cccgtcccgg ccgtgcccgt gtcggtccgc     300
gctcggcaac gaggcggccc gcgctgctga gtcccctgga cacccgacac cctgtcggcc     360
ctttgtttat tcatcccgaa atctcatctg cccccacggc cgactgcgct gcgccgcccg     420
gatatatata cccatcgtta tcgatcgatc gatcgcgtca ctcacgggta gctcatggtc     480
gagcgtagca tgcaggaact tatttgccgt gcgctcccag gtctccgctc gcgtgccttc     540
cagtctgtct cacactagct gctgtgggac gatcgaagtg ggtgtgtcag ctagctagct     600
gcgccgtgac cacgcacatg accgcagtgc gcgcggggct gatcaaggga aagtgatccc     660
atg                                                                  663
```